(12) United States Patent
Wallace et al.

(10) Patent No.: US 8,178,578 B2
(45) Date of Patent: May 15, 2012

(54) CHEMICAL COMPOUNDS

(75) Inventors: Timothy William Wallace, Stockport (GB); David John Edwards, Manchester (GB); John Anthony Hadfield, Cheshire (GB)

(73) Assignee: The University of Manchester, Manchester (GB)

( * ) Notice: Subject to any disclaimer, the term of this patent is extended or adjusted under 35 U.S.C. 154(b) by 430 days.

(21) Appl. No.: 12/520,372

(22) PCT Filed: Dec. 19, 2007

(86) PCT No.: PCT/GB2007/004890
§ 371 (c)(1),
(2), (4) Date: Jun. 19, 2009

(87) PCT Pub. No.: WO2008/075048
PCT Pub. Date: Jun. 26, 2008

(65) Prior Publication Data
US 2010/0016261 A1 Jan. 21, 2010

(30) Foreign Application Priority Data
Dec. 20, 2006 (GB) .................... 0625371.0

(51) Int. Cl.
*A61K 31/33* (2006.01)
*A61K 31/357* (2006.01)
*C07D 313/10* (2006.01)
*C07D 493/04* (2006.01)

(52) U.S. Cl. ........ 514/450; 514/100; 549/213; 549/220; 549/354

(58) Field of Classification Search .................. 549/354, 549/220; 514/450, 100
See application file for complete search history.

(56) References Cited

U.S. PATENT DOCUMENTS
4,996,237 A 2/1991 Pettit et al.

OTHER PUBLICATIONS

United Kingdom Search Report for Application No. GB0625371.0 dated Apr. 18, 2007 (1 page).
Galbraith et al., Combretastatin A4 Phosphate has tumor Antivascular Activity in Rat and Man as Demonstrated by Dynamic Magnetic Resonance Imaging, Journal of Clinical Oncology, Aug. 1, 2003, pp. 2831-2842, vol. 21, No. 15, American Society of Clinical Oncology.
Galbraith et al., Effects of Combretatstatin A4 Phosphate on Endothelial Cell Morphology in Vitro and Relationship in Tumour Vascular Targeting Activity in Vivo, Anticancer Research, 2001, pp. 93-102, vol. 21, supplied by The British Library.
Tozer, Measuring tumour vascular response to antivascular and antiangiogenic drugs, The British Journal of Radiology, Special Issue 2003, pp. S23-S35, vol. 76, The British Institute of Radiology.
Grosios et al., In vivo and in vitro evaluation of combretatstatin A-4 and its sodium phosphate prodrug, British Journal of Cancer, 1999, pp. 1318-1327, vol. 81, No. 8, Cancer Research Campaign.
Kochetkov et al., Schizandrin-Lignan of Unusual Structure, Tetrahedron Letters, 1961, pp. 730-734, No. 20, Pergamon Press Ltd., Great Britain, supplied by The British Library.
Insole, Buttressing and Electronic Effects of meta- and para-Methoxy Substituents on the Configurational Stability of 5,7-Dihydro-1,11-dimethoxydibenz[c,e]oxepine, Journal of Chemical Research (S), 1990, pp. 378-379, vol. 12, supplied by The British Library.
Takada et al., Oxidative Biaryl Coupling Reaction of Phenol Ether Derivatives Using a Hypervalent Iodine(III) Reagent, Journal of Organic Chemistry, 1998, pp. 7698-7706, vol. 63, supplied by The British Library.
Linden et al., (P,M)-1,2,3,9,10,11-Hexamethoxy-5,7-dihydrodibenz[c,e]oxepine and (P,M)-1,11-dimethyl-5,5,7,7-tetraphenyl-5,7-dihydrodibenz[c,e]oxepine, Acta Crystallographica Section C, Crystal Structure Communications, 2004, pp. 223-225, vol. 60, International Union of Crystallography, supplied by The British Library.
Edwards et al., Fine-tuning of biaryl dihedral angels: structural characterization of five homologous three-atom bridged biphenyls by X-ray crystallography, Acta Crystallographica Section B, Structural Science, 2005, pp. 335-345, vol. B61, International Union of Crystallography, Great Britain, supplied by The British Library.
International Search Report from PCT/GB2007/004890 dated Aug. 13, 2008 (7 pages).
Written Opinion from PCT/GB2007/004890 dated Aug. 13, 2008 (9 pages).
Abe, H., et al.: "Enantioselective Construction of Biaryl Part in the Synthesis of Stegane Related Compounds", Tetrahedron Letters, vol. 45, (2004), pp. 2327-2329. Yoshiki Kashiwada, et al.: "New Hexahydroxybiphenyl Derivatives as Inhibitors of Protein Kinase C", Journal of Medicinal Chemistry, vol. 37, (1994), pp. 195-200.
Buttner, F., et al.: "Two Novel Series of Allocolchicinoids with Modified Seven Membered B-Rings: Design, Synthesis, Inhibition of Tubulin Assembly and Cytotoxicity", Bioorganic & Medicinal Chemistry, vol. 13, (2005), pp. 3497-3511.
Joncour, "Biaryl Axis as a Stereochemical Relay for the Enantioselective Synthesis of a Antimicrotubule Agents", Angew. Chem. Int. Ed., (2006), vol. 45, pp. 4149-4152.

*Primary Examiner* — Bernard Dentz
(74) *Attorney, Agent, or Firm* — Michael Best & Friedrich LLP

(57) ABSTRACT

A compound of formula (I) is described; wherein the substituents are as defined in the text and wherein the compound is intended for use in the production of a vascular damaging effect in a warm-blooded animal.

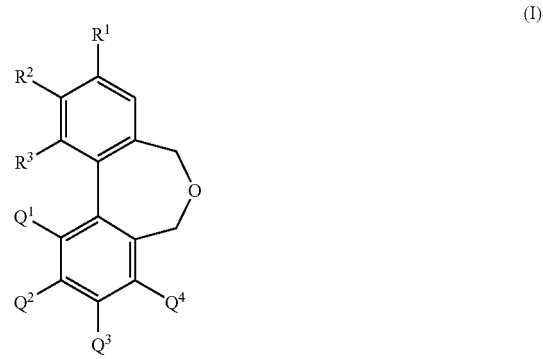

(I)

28 Claims, 1 Drawing Sheet

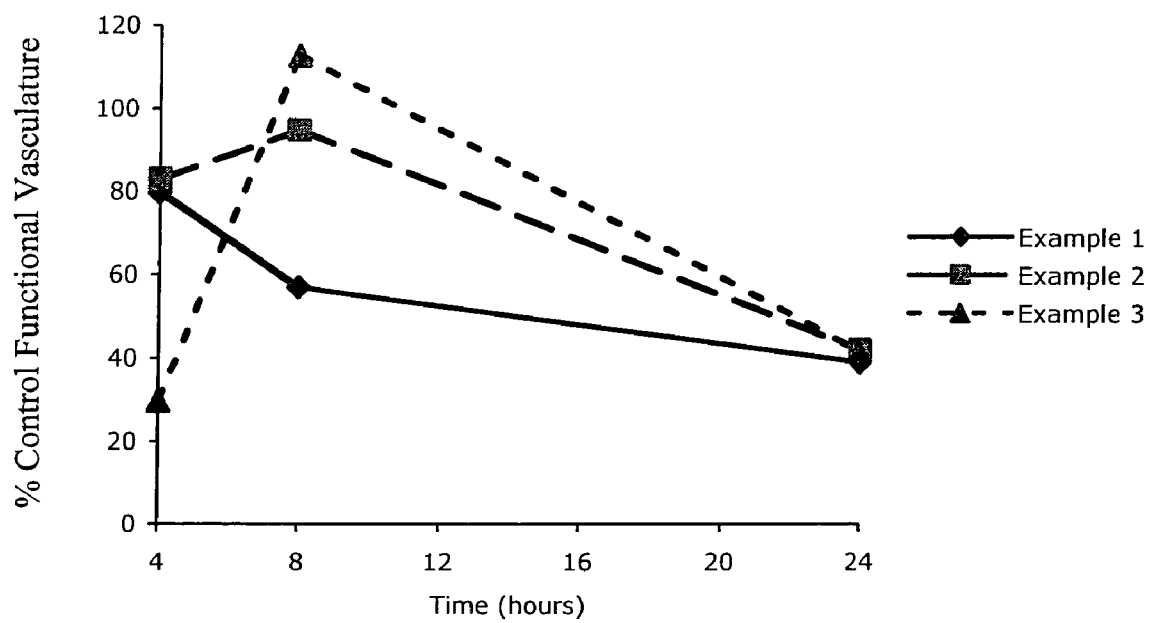

CHEMICAL COMPOUNDS

CROSS-REFERENCE TO RELATED APPLICATIONS

This patent application is a national stage filing under 35 U.S.C, 371 of International Application No. PCT/GB2007/004890, filed Dec. 19, 2007, which claims foreign priority to Great Britain Patent Application No. 0625371.0, filed Dec. 20, 2006, the disclosures of which are incorporated by reference herein in their entireties. Priority to each application is hereby claimed.

The present invention relates to certain compounds or pharmaceutically acceptable salts thereof for use in the production of a vascular damaging effect in a warm-blooded animal and to certain novel compounds or pharmaceutically acceptable salts thereof, to processes for the preparation of the novel compounds and to uses of the novel compounds as medicaments, for example for the treatment of a range of diseases, such as cancers (especially solid tumours), macular degeneration and proliferative retinopathy.

Typically, many cancers, including malignant tumours, are treated using chemotherapy and/or radiotherapy, but such treatments can be inherently toxic to the patient and poorly targeted. Additionally, cancers can become resistant to many of the typical chemotherapy drugs. There is, therefore, a need for new anti-cancer treatments that have the potential to overcome or reduce the disadvantages associated with current treatments and that are effective in the treatment of a range of cancers.

The term tumour is primarily used to denote abnormal growth of tissue. A tumour can be either malignant or benign. A malignant tumour starts from a single cell that has turned cancerous, which cell then goes on to divide and make more cancerous cells which form the tumour. For a tumour to continue to grow, it must develop its own blood supply (i.e. tumour vasculature) so as to obtain oxygen and nourishment for the new and dividing cells. Cancer cells make chemicals that stimulate tiny blood vessels to grow around them, which branch off from the existing blood vessels. This ability for cancer cells to stimulate the growth of blood vessels is called angiogenesis.

New classes of therapeutic agents for use in cancer treatment have been developed that act by depriving tumours of the blood supply or vasculature required for growth. There are two categories of compounds that act in this way. These are anti-angiogenic agents and vascular targeting agents. Anti-angiogenic agents inhibit the formation of new blood vessels. Vascular targeting agents are designed to cause a rapid and selective shutdown of the existing blood vessels of tumours and cause tumour cell death from ischemia and extensive hemorrhagic necrosis.

There are broadly two types of vascular targeting agents, small molecules and ligand-based agents.

The ligand-based vascular targeting agents use antibodies, peptides or growth factors that bind selectively to tumour versus normal vessels to target tumours with agents that occlude blood vessels. The ligand-based vascular targeting agents include fusion proteins (for example vascular endothelial growth factor linked to the plant toxin gelonin), immunotoxins (for example monoclonal antibodies to endoglin conjugated to ricin A), antibodies linked to cytokines, liposomally encapsulated drugs, and gene therapy approaches.

Small-molecule vascular targeting agents may act by disrupting the vasculature in tumour cells, for example by exploiting structural and physiological differences between normal and pathologic vasculature to selectively disrupt and occlude vessels within the tumour.

Proliferating endothelial cells, such as those of the tumour neovasculature, rely on a cytoskeleton to maintain vessel shape. The cytoskeleton includes microtubules, which are polymers of α- and β-tubulin dimers or subunits. There exists an equilibrium between the dimers/subunits and the tubulin polymer (i.e. microtubules). Disruption of the tubulin polymers or microtubules, and the processes by which they are formed, destabilises the cytoskeleton and results in the damage or destruction of the vasculature. This disruption can, for example, be brought about by a small molecule binding or interacting with tubulin or the cellular machinery regulating the process of polymerisation.

The most well known small molecule vascular targeting agents are combretastatin A4 (CA4) and combretastatin A4 phosphate (CA4P).

Combretastatin A4 is a natural product and was isolated from the bark and stem wood of the South African tree, Combretum caffrum (see U.S. Pat. No. 4,996,237). Combretastatin A4 phosphate is the disodium phosphate salt of combretastatin A4 and is a pro-drug that is converted to combretastatin A4 in a warm-blooded animal (such as man).

Combretastatin A4 and combretastatin A4 phosphate are stilbene compounds and their structures are as follows (where "Me" represents methyl):

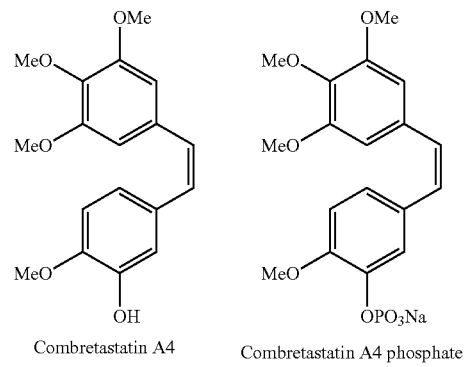

Combretastatin A4   Combretastatin A4 phosphate

Combretastatin A4 has been shown to be capable of selectively destroying tumour vasculature. It disrupts the microtubular structures within immature endothelial cells (which lack the structural protein actin) lining the newly forming tumour-associated blood vessels. This triggers a rounding of the shape of these cells, in turn blocking the flow of blood to a tumour and depriving it of oxygen and nutrients essential for its survival and thus causing tumour cell death (see, for example, *J. Clin. Oncology*, 2003, 21, 2831-42, Combretastatin A4 Phosphate Has Tumor Antivascular Activity in Rat and Man as Demonstrated by Dynamic Magnetic Resonance Imaging, Susan M. Galbraith et al.; Anticancer Res., 2001, 21, 93-102, Effects of combretastatin A4 phosphate on endothelial cell morphology in vitro and relationship to tumour vascular targeting activity in vivo, Galbraith S. M. et al.; Brit. J. Radiobiology, 2003, 76, S123-S125, Measuring tumour vascular response to antivascular and antiangiogenic drugs, Tozer, G. M.; and Brit. J. Cancer, 1999, 81, 1318-27, In vivo and in vitro evaluation of combretastatin A-4 and its sodium phosphate prodrug, Grosios K. et al.).

Combretastatin A4 and combretastatin A4 phosphate are currently being tested in clinical trials for anti-tumour activity. Some undesirable side effects have been identified in these clinical trials, which include causing temporary blindness and cardiotoxicity.

Combretastatin A4 phosphate has also shown the ability to suppress development and induce regression of recently formed abnormal blood vessels that occur in certain eye diseases and is being studied in clinical trials for the treatment of myopic macular degeneration. Macular degeneration is an eye disorder that causes loss of central vision and is a major cause of blindness.

Other small molecule vascular targeting agents that are known are combretastatin A1 and its prodrug which is known as OX14503. OX14503 is currently undergoing clinical trials as an anti-tumour agent. Combretastatin A1 and combretastatin A1 prodrug are again stilbene compounds and their structures are as follows (where "Me" represents methyl):

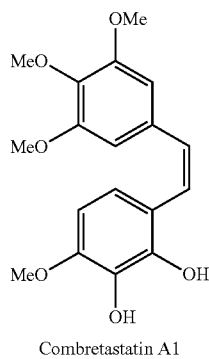
Combretastatin A1

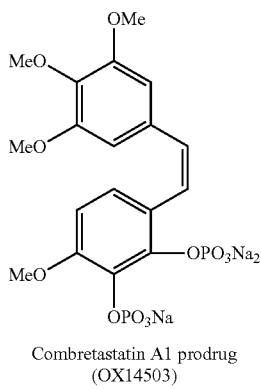
Combretastatin A1 prodrug (OX14503)

Other known small molecule vascular targeting agents that have undergone clinical trials are AVE8062 and ZD6126. AVE8062 is another stilbene compound. ZD6126 is a phosphate prodrug of N-acetylcolchinol. The structures of AVE8062 and ZD6126 are as follows (where "Me" represents methyl):

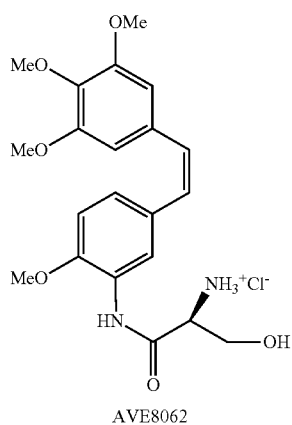
AVE8062

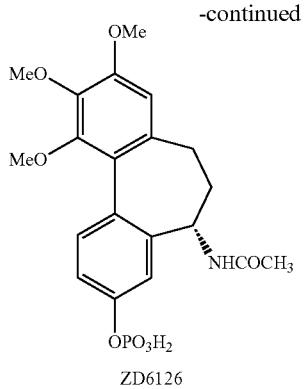
ZD6126

Additionally, a publication by Baudoin et al. (Joncour A., Décor, A., Thoret, S., Chiaroni, A., Baudoin, O., Angew. Chem. Int. Ed., 2006, 45, 4149-4152) discloses several biaryl analogues of colchinol containing a heterocyclic bridge and a method for the enantioselective synthesis of these analogues. The compounds disclosed in Baudion et al. have the following general formula (where "Me" represents methyl):

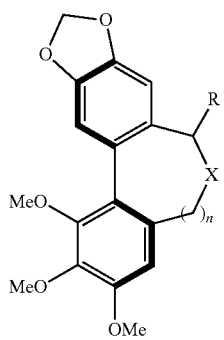

where R is methyl, n is 1 and X is O or NH, or R is ethyl, n is 1 and X is O, or R is methyl, n is 2 and X is O. There is no disclosure in Baudoin et al. of a compound in which the group R on the heterocyclic bridge is hydrogen. Baudoin et al. suggests that the compounds it discloses could be useful as vascular targeting agents.

Several documents (Kochetkov et al., Tetrahedron Letters, 20, 1961, 720-734; Insole, J. Chem. Research (S), 12, 1990, 378-379; Kashiwada et al, J. Med. Chem., 37, 1994, 195-200; Takada et al, J. Org. Chem., 63, 1998, 7698-7706; Linden et al, Acta Cryst., C60, 2004, o223-o225; and Edwards et al, Acta Cryst., B61, 2005, 335-345) disclose further biphenyl compounds, but these documents do not disclose the use of the compounds for producing a vascular damaging effect in a warm-blooded animal (such as man).

In general vascular targeting agents are believed to be able to selectively and rapidly induce the shutdown of blood flow to a tumour, whilst leaving normal vasculature intact. They are inherently less toxic to patients than conventional therapies and many of the vascular targeting agents that have been investigated in clinical trials have been found to act at doses well below their maximum tolerated dose. Additionally, vascular targeting agents are believed to be less susceptible over time to tumour resistance compared to conventional therapies and can be used to treat a wide range of tumours, including large-sized tumours. The cells that make up the blood vessels as discussed above are not themselves malignant and it is believed, therefore, that they are unlikely to undergo genetic changes that give rise to resistance to direct-acting anti-tumour agents.

None of the aforementioned small molecule vascular targeting agents have yet been authorised by the regulatory authorities for use as prescribed medicines and alternative and potentially improved agents are highly desired for use in treating a range of diseases, including cancers (especially malignant tumours), macular degeneration and proliferative retinopathy. Thus, there remains a need to find further compounds with good in vivo activity as vascular targeting agents, as well as improved pharmacological characteristics compared with known small molecule vascular targeting agents. Improved pharmacological characteristics that are desirable include improved solubility, improved bioavailability and/or fewer incidences of undesirable side effects.

One aspect of the present invention relates to the use of certain compounds or pharmaceutically acceptable salts thereof in the production of a vascular damaging effect in a warm-blooded animal (such as man). Accordingly, a first aspect of the present invention provides a compound of the Formula I:

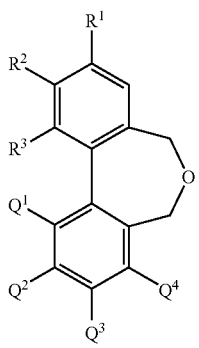

or a pharmaceutically acceptable salt thereof
wherein:
$R^1$, $R^2$ and $R^3$ each independently represent (1-4C)alkoxy;
$Q^1$, $Q^2$, $Q^3$ and $Q^4$ each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

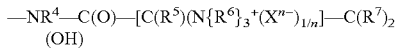

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or
any one of $Q^2$ and $Q^3$ or $Q^3$ and $Q^4$ represents a methylenedioxy group;
and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents;
for the production of a vascular damaging effect in a warm-blooded animal (such as man).

There is further provided the use a compound of the Formula I, or a pharmaceutically acceptable salt thereof, as defined above in the manufacture of a medicament for use in the production of a vascular damaging effect in a warm-blooded animal (such as man).

There is further provided a method for producing a vascular damaging effect in a warm-blooded animal (such as man) in need of such treatment which comprises administering to said animal an effective amount of a compound of the Formula I, or a pharmaceutically acceptable salt thereof, as defined above.

Another aspect of the present invention relates to certain novel compounds or pharmaceutically acceptable salts thereof, to processes for their preparation and to their use for example as medicaments for the treatment of a range of diseases, including (but not limited to) cancers (especially solid tumours), macular degeneration and proliferative retinopathy. Accordingly, a second aspect of the present invention provides a compound of the Formula I:

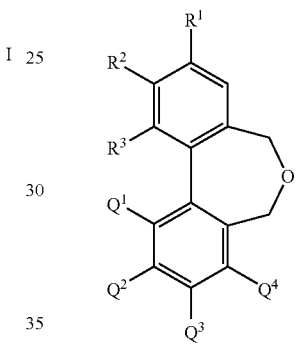

or a pharmaceutically acceptable salt thereof
wherein:
$R^1$, $R^2$ and $R^3$ each independently represent (1-4C)alkoxy;
$Q^1$, $Q^2$, $Q^3$ and $Q^4$ each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

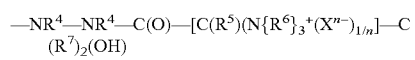

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or
any one of $Q^2$ and $Q^3$ or $Q^3$ and $Q^4$ represents a methylenedioxy group;
and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents;
provided that when $Q^1$ represents hydrogen or methoxy and $Q^4$ represents hydrogen, then $Q^2$ and $Q^3$ do not both represent methoxy.

BRIEF DESCRIPTION OF THE DRAWING

FIG. 1 shows data on the destruction of functional vasculature in DLD-1 tumours for several of the compounds of the invention.

It is believed that the compounds of the Formula I meet the objectives set out above. It is believed that the compounds of the Formula I possess good in vivo activity as vascular targeting agents and provide a vascular damaging effect, as well as improved pharmacological characteristics compared with known small molecule vascular targeting agents.

It is believed that the ability of the compounds of the Formula I to bind or interact with tubulin (and to act as vascular targeting agents) is aided by the absence of any non-hydrogen substituents on the —$CH_2$—O—$CH_2$— bridge (i.e. which bridge contains no substituents on the —$CH_2$— groups). The absence of any such non-hydrogen substituents maximises the conformational freedom of the —$CH_2$—O—$CH_2$— bridge, thus maximising the ability of the compounds of the Formula I to adopt the conformation required for the binding interaction with tubulin.

Further, without wishing to be bound by any theory, it is believed that in the compounds of the Formula I the biaryl axis (i.e. the bond linking the two benzene rings) is fully flexible when there are no substituents on the —$CH_2$— groups of the —$CH_2$—O—$CH_2$— bridge, with whose movement the compounds are obliged to synchronise, this effect being maximal when $Q^1$ represents a suitably sized group to allow for the stereochemical inversion of the axis (such as when $Q^1$ represents hydrogen or fluoro, especially hydrogen). The flexibility of the biaryl axis aids the ability of the compounds to bind to or interact with tubulin and to act as vascular targeting agents.

Additionally, the compounds of the Formula I are believed to possess little or no toxicity to patients at the doses at which they may be administered, therefore causing fewer incidences of undesirable side effects compared to conventional therapies. The compounds further are active to provide a vascular damaging effect at doses well below their maximum tolerated dose, are less susceptible over time to tumour resistance compared to conventional therapies and can be used to treat a wide range of tumours, including large-sized tumours.

In this specification the generic term "alkyl" includes both straight-chain and branched-chain alkyl groups such as propyl, isopropyl and tert-butyl. However, references to individual alkyl groups such as "propyl" are specific for the straight-chain version only and references to individual branched-chain alkyl groups such as "isopropyl" are specific for the branched-chain version only. An analogous convention applies to other generic terms, for example (1-4C)alkoxy includes methoxy and ethoxy, (1-4C)alkylamino includes methylamino, ethylamino and isopropylamino and di-[(1-4C)alkyl]amino includes dimethylamino, diethylamino and N-isopropyl-N-methylamino.

In this specification reference to a (1-4C)alkyl group is to be understood to refer to alkyl groups containing up to 4 carbon atoms. Similarly, reference to a (1-2C)alkyl group refers to alkyl groups containing up to 2 carbon atoms, such as methyl and ethyl. A similar convention is adopted for the other groups listed herein.

Suitable values for any of the R groups ($R^1$ to $R^9$) and for any of the Q groups ($Q^1$ to $Q^4$) include:—

| | |
|---|---|
| for halogeno | fluoro, chloro, bromo and iodo; |
| for (1-4C)alkyl: | methyl, ethyl, propyl, isopropyl, isobutyl, sec-butyl and tert-butyl; |
| for (2-4C)alkenyl: | vinyl, isopropenyl, allyl and but-2-enyl; |
| for (2-4C)alkynyl: | ethynyl, 2-propynyl and but-2-ynyl; |
| for (1-4C)alkoxy: | methoxy, ethoxy, propoxy, isopropoxy and butoxy; |
| for (1-4C)alkylamino: | methylamino, ethylamino, propylamino, isopropylamino and butylamino; |
| for di-[(1-4C)alkyl]amino: | dimethylamino, diethylamino, N-ethyl-N-methylamino and diisopropylamino; |
| for (1-4C)alkylthio: | methylthio, ethylthio and propylthio; |
| for (1-4C)alkylsulfonyl: | methylsulfonyl and ethylsulfonyl; and |
| for (1-4C)alkylsulfonyloxy: | methylsulfonyloxy and ethylsulfonyloxy. |

When in this specification reference is made to any $CH_2$ or $CH_3$ group within a $R^1$, $R^2$, $R^3$, $Q^1$, $Q^2$, $Q^3$ and/or $Q^4$ substituent optionally bearing on each said $CH_2$ or $CH_3$ group one or more halogeno or hydroxy substituents, there are suitably 1 or 2 halogeno or hydroxy substituents present on each said $CH_2$ group and there are suitably 1, 2 or 3 such substituents present on each said $CH_3$ group. For example, should a $CH_3$ group within a (1-4C)alkoxy group $R^1$, $R^2$ and/or $R^3$ bear a hydroxy substituent, suitable substituents so formed include hydroxy-(1-4C)alkoxy substituents, such as hydroxy-methoxy, 2-hydroxy-ethoxy, 3-hydroxypropoxy or 4-hydroxy-butoxy substituents. Substituent groups, such as $R^4$, $R^5$, $R^6$, $R^7$, $R^8$ and $R^9$, within the $R^1$, $R^2$, $R^3$, $Q^1$, $Q^2$, $Q^3$ and/or $Q^4$ substituents, also may optionally bear on any $CH_2$ or $CH_3$ group one or more halogeno or hydroxy substituents.

For the avoidance of doubt, by the term "alkali metal" we mean those metals listed in Group 1 of the Periodic Table of Elements (according to established IUPAC nomenclature), i.e. lithium (Li), sodium (Na), potassium (K), rubidium (Rb), caesium (Cs) and francium (Fr). In particular, the alkali metal is selected from lithium (Li), sodium (Na) and potassium (K), and especially the alkali metal is sodium (Na).

An alkali metal phosphato group, therefore, is a group of the formula —O—$PO_3M_2$, where M represents an alkali metal ion. For example, a suitable alkali metal phosphato group is disodium phosphate.

A thiol group is a group of the formula —SH.

As herein defined, in the group of the formula:

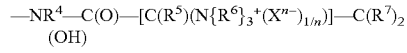

(wherein $R^4$, $R^5$, $R^6$ and $R^7$ each are as defined herein), $X^{n-}$ represents a suitable anion and n is 1 or 2. As the skilled person would appreciate, $X^{n-}$ may represent any suitable anion and n represents the valency of the anion and is 1 or 2. In particular, n is 1.

When n is 1, suitable anions $X^-$ include halide ions, such as chloride, bromide and iodide. For example, when n is 1, the group of the formula —$NR^4$—C(O)—[C($R^5$)(N$\{R^6\}_3{}^+$ $X^-$)]—C($R^7$)$_2$(OH) may represent —NH—C(O)—[C(H) ($NH_3{}^+Cl^-$)]—$CH_2$OH.

When n is 2, suitable anions $X^{2-}$ include sulfate and phosphate. As the skilled person would appreciate, when n is 2 and a divalent anion ($X^{2-}$) is included, then the divalent anion balances the charge of two positive charges associated with the N$\{R^6\}_3{}^+$ groups in the group of the formula —$NR^4$—C (O)—[C($R^5$)(N$\{R^6\}_3{}^+X^{n-}$)]—C($R^7$)$_2$(OH).

References herein to any one of $Q^2$ and $Q^3$ or $Q^3$ and $Q^4$ representing a methylenedioxy group, relate to forming a methylenedioxy bridge on the phenyl ring of the compounds of the Formula I. For example, when $Q^2$ and $Q^3$ represent a methylenedioxy group, the following compounds of the Formula I are provided:

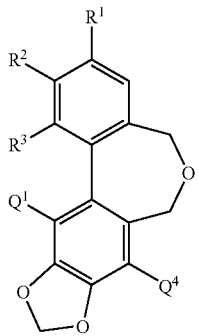

I wherein $R^1$, $R^2$, $R^3$, $Q^1$ and $Q^4$ are as herein defined, or a pharmaceutically acceptable salt thereof.

As the skilled person would appreciate, in the compounds of the Formula I, the biaryl axis (i.e. the bond linking the two benzene rings) may adopt two possible helical configurations, which configurations are designated "aR" or "aS". The present invention includes all such configurations and mixtures thereof.

As discussed above, it is believed that the biaryl axis in the compounds of the Formula I, which contain no non-hydrogen substituents on the —$CH_2$—O—$CH_2$— bridge, is fully flexible when $Q^1$ represents a suitably sized group, such as hydrogen, and that this flexibility aids the ability of the compounds to bind to or interact with tubulin and to act as vascular targeting agents.

Where the compounds of the Formula I contain one or more asymmetrically substituted carbon atoms (i.e. chiral centres), the aspects of the present invention includes all stereoisomers (including enantiomers and diastereomers) and mixtures (including racemic mixtures) thereof. Tautomers and mixtures thereof are also included within the scope of the present invention.

The present invention also includes all solvated (for example hydrated) as well as unsolvated forms of the compounds of the Formula I, especially those forms that produce a vascular damaging effect in a warm-blooded animal (such as man).

The present invention also includes all polymorphic forms of the compounds of the Formula I, especially those forms that produce a vascular damaging effect in a warm-blooded animal (such as man).

The compounds of the Formula I may be provided as pharmaceutically acceptable salts and the present invention includes all such salts. Suitable pharmaceutically acceptable salts include alkali or alkaline earth metal salts for compounds that are sufficiently acidic and halide, and phosphate and sulfate salts for compounds that are sufficiently basic.

In accordance with the first aspect of the present invention, in the compound of the Formula I, or a pharmaceutically acceptable salt thereof, $Q^1$, $Q^2$, $Q^3$ and $Q^4$ may each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, an alkali metal phosphato group, or a group of the formula:

$$-NR^4-C(O)-[C(R^5)(N\{R^6\}_3^+(X^{n-})_{1/n})]-C(R^7)_2$$
$$(OH)$$

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

$$-BR^8R^9$$

wherein $R^8$ and $R^9$ each independently represent hydrogen, hydroxy or (1-4C)alkoxy, or any one of $Q^2$ and $Q^3$ or $Q^3$ and $Q^4$ represents a methylenedioxy group;

and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents.

In accordance with the first aspect of the present invention, in the compound of the Formula I, or a pharmaceutically acceptable salt thereof, $Q^1$, $Q^2$, $Q^3$ and $Q^4$ may each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

$$-NR^4-C(O)-[C(R^5)(N\{R^6\}_3^+(X^{n-})_{1/n})]-C(R^7)_2$$
$$(OH)$$

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

$$-BR^8R^9$$

wherein $R^8$ and $R^9$ each independently represent hydrogen, hydroxy or (1-4C)alkoxy, or and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents.

Further, in accordance with the first aspect of the present invention, in the compound of the Formula I, or a pharmaceutically acceptable salt thereof, $Q^1$, $Q^2$, $Q^3$ and $Q^4$ may each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, an alkali metal phosphato group, or a group of the formula:

$$-NR^4-C(O)-[C(R^5)(N\{R^6\}_3^+(X^{n-})_{1/n})]-C(R^7)_2$$
$$(OH)$$

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents.

Further, in accordance with the first aspect of the present invention, in the compound of the Formula I, or a pharmaceutically acceptable salt thereof, $Q^1$, $Q^2$, $Q^3$ and $Q^4$ may each independently represent hydrogen, halogeno, hydroxy, (1-4C)alkoxy, amino, (1-4C)alkylamino, di-[(1-4C)alkyl]amino, an alkali metal phosphato group or a group of the formula:

—NR⁴—C(O)—[C(R⁵)(N{R⁶}₃⁺X⁻)]—C(R⁷)₂(OH)

wherein $R^4$, $R^5$, $R^6$ and $R^7$ each independently represent hydrogen or (1-4C)alkyl (especially hydrogen) and $X^-$ represents a suitable anion, or any one of $Q^2$ and $Q^3$ or $Q^3$ and $Q^4$ may represent a methylenedioxy group;

and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy substituents.

Further, in accordance with the first aspect of the present invention, in the compound of the Formula I, or a pharmaceutically acceptable salt thereof, $Q^1$, $Q^2$, $Q^3$ and $Q^4$ may each independently represent hydrogen, halogeno, hydroxy, (1-2C)alkoxy, amino, or a group of the formula:

—NR⁴—C(O)—[C(R⁵)(N{R⁶}₃⁺X⁻)]—C(R⁷)₂(OH)

wherein $R^4$, $R^5$, $R^6$ and $R^7$ each independently represent hydrogen or (1-2C)alkyl (especially hydrogen) and $X^-$ represents a suitable anion, or any one of $Q^2$ and $Q^3$ or $Q^3$ and $Q^4$ may represent a methylenedioxy group.

Further, in accordance with the first aspect of the present invention, in the compound of the Formula I, or a pharmaceutically acceptable salt thereof, $Q^1$, $Q^2$, $Q^3$ and $Q^4$ may each independently represent hydrogen, hydroxy or (1-4C)alkoxy (especially (1-2C)alkoxy, such as methoxy), or any one of $Q^2$ and $Q^3$ or $Q^3$ and $Q^4$ may represent a methylenedioxy group.

Further, in accordance with the first aspect of the present invention, in the compound of the Formula I, or a pharmaceutically acceptable salt thereof, $Q^1$, $Q^2$, $Q^3$ and $Q^4$ may each independently represent hydrogen, halogeno, hydroxy, (1-4C)alkoxy, amino, (1-4C)alkylamino, di-[(1-4C)alkyl]amino, an alkali metal phosphato group or a group of the formula:

—NR⁴—C(O)—[C(R⁵)(N{R⁶}₃⁺X⁻)]—C(R⁷)₂(OH)

wherein $R^4$, $R^5$, $R^6$ and $R^7$ each independently represent hydrogen or (1-4C)alkyl (especially hydrogen) and $X^-$ represents a suitable anion;

and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy substituents.

Further, in accordance with the first aspect of the present invention, in the compound of the Formula I, or a pharmaceutically acceptable salt thereof, $Q^1$, $Q^2$, $Q^3$ and $Q^4$ may each independently represent hydrogen, halogeno, hydroxy, (1-2C)alkoxy, amino, or a group of the formula:

—NR⁴—C(O)—[C(R⁵)(N{R⁶}₃⁺X⁻)]—C(R⁷)₂(OH)

wherein $R^4$, $R^5$, $R^6$ and $R^7$ each independently represent hydrogen or (1-2C)alkyl (especially hydrogen) and $X^-$ represents a suitable anion.

Further, in accordance with the first aspect of the present invention, in the compound of the Formula I, or a pharmaceutically acceptable salt thereof, $Q^1$, $Q^2$, $Q^3$ and $Q^4$ may each independently represent hydrogen, hydroxy or (1-4C)alkoxy (especially (1-2C)alkoxy, such as methoxy).

Further, in accordance with the first aspect of the present invention, in the compound of the Formula I, or a pharmaceutically acceptable salt thereof, preferably at least one of $Q^1$, $Q^2$, $Q^3$ and $Q^4$ is hydrogen and at least one of $Q^1$, $Q^2$, $Q^3$ and $Q^4$ is a group other than hydrogen as defined above.

In accordance with the first aspect of the present invention, the vascular damaging effect may be produced at least in part by inhibition of tubulin assembly (or polymerisation) into microtubules thereby interfering with cellular tubulin-microtubule equilibrium. As the skilled person would appreciate, the cellular tubulin-microtubule equilibrium as discussed above regulates the maintenance of the vessel shape.

In accordance with the first aspect of the present invention, the compound of the Formula I, or a pharmaceutically acceptable salt thereof, may be provided for the treatment of a disease or medical condition in which the damage and/or destruction of the vasculature in a warm-blooded animal (such as man) has an effect.

There is further provided the use a compound of the Formula I, or a pharmaceutically acceptable salt thereof, as defined above in the manufacture of a medicament for use in the treatment of a disease or medical condition in which the damage and/or destruction of the vasculature in a warm-blooded animal (such as man) has an effect.

There is further provided a method for treating a disease or medical condition in which the damage and/or destruction of the vasculature in a warm-blooded animal (such as man) has an effect which comprises administering to said animal an effective amount of a compound of the Formula I, or a pharmaceutically acceptable salt thereof, as defined above.

In accordance with the first aspect of the present invention, the compound of the Formula I, or a pharmaceutically acceptable salt thereof, may be provided for the treatment of a vascular proliferative disease or medical condition in a warm-blooded animal (such as man).

There is further provided the use a compound of the Formula I, or a pharmaceutically acceptable salt thereof, as defined above in the manufacture of a medicament for use in the treatment of a vascular proliferative disease or medical condition in a warm-blooded animal (such as man).

There is further provided a method for treating a vascular proliferative disease or medical condition in a warm-blooded animal (such as man) in need of such treatment which comprises administering to said animal an effective amount of a compound of the Formula I, or a pharmaceutically acceptable salt thereof, as defined above.

The disease or medical condition in which the damage and/or destruction of the vasculature has an effect and/or the vascular proliferative disease or medical condition may be selected from one or more of a cancer, macular degeneration, proliferative retinopathy (such as proliferative diabetic retinopathy), psoriasis and/or endometriosis. In particular, the disease or medical condition may be selected from a cancer, macular degeneration and/or proliferative retinopathy (such as proliferative diabetic retinopathy), for example the disease or medical condition may be selected from a cancer and macular degeneration.

More particularly, the vascular proliferative disease or medical condition may be a cancer. The cancer may, for example, be selected from one or more of leukaemias, colorectal, cervical, head and neck, lung, ovarian, pancreatic, thyroid, prostate, bladder, brain, breast, liver, stomach, oesophageal and/or skin cancers. The cancer may for example be a cancer involving a solid tumour, such as a cancer selected from one or more of colorectal, cervical, head and neck, lung, ovarian, pancreatic, thyroid, prostate, bladder, brain, breast, liver, stomach, oesophageal and/or skin cancers.

The vascular proliferative disease or medical condition may be macular degeneration.

The vascular proliferative disease or medical condition may be proliferative retinopathy (such as proliferative diabetic retinopathy).

In the second aspect of the present invention, in one embodiment, $Q^2$ and $Q^3$ may not both represent methoxy when $Q^4$ represents hydrogen and when $Q^1$ represents any group as herein defined (including hydrogen and methoxy).

In the second aspect of the present invention, $Q^1$, $Q^2$, $Q^3$ and $Q^4$ may each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, an alkali metal phosphato group, or a group of the formula:

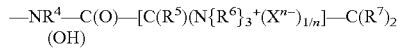
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or
any one of $Q^2$ and $Q^3$ or $Q^3$ and $Q^4$ may represent a methylenedioxy group;
and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy substituents;
provided that when $Q^1$ represents hydrogen or methoxy and $Q^4$ represents hydrogen, then $Q^2$ and $Q^3$ do not both represent methoxy.

In the second aspect of the present invention, $Q^1$, $Q^2$, $Q^3$ and $Q^4$ may each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

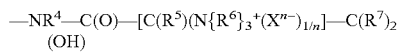
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy,
and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents;
provided that when $Q^1$ represents hydrogen or methoxy and $Q^4$ represents hydrogen, then $Q^2$ and $Q^3$ do not both represent methoxy.

In the second aspect of the present invention, $Q^1$, $Q^2$, $Q^3$ and $Q^4$ may each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, an alkali metal phosphato group, or a group of the formula:

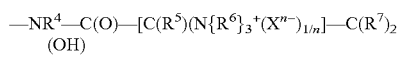
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy,
and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy substituents;
provided that when $Q^1$ represents hydrogen or methoxy and $Q^4$ represents hydrogen, then $Q^2$ and $Q^3$ do not both represent methoxy.

In the second aspect of the present invention, $Q^1$, $Q^2$, $Q^3$ and $Q^4$ may each independently represent hydrogen, halogeno, hydroxy, thiol, (2-4C)alkynyl, (1-4C)alkoxy, amino, (1-4C)alkylsulfonyloxy, an alkali metal phosphato group, or a group of the formula:

wherein $R^8$ and $R^9$ each independently represent hydrogen, hydroxy or (1-4C)alkoxy, or
any one of $Q^2$ and $Q^3$ or $Q^3$ and $Q^4$ (especially $Q^2$ and $Q^3$) may represent a methylenedioxy group;
and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy substituents;
provided that when $Q^1$ represents hydrogen or methoxy and $Q^4$ represents hydrogen, then $Q^2$ and $Q^3$ do not both represent methoxy.

In the second aspect of the present invention, $Q^1$, $Q^2$, $Q^3$ and $Q^4$ may each independently represent hydrogen, halogeno, hydroxy, thiol, (2-4C)alkynyl, (1-4C)alkoxy, amino, (1-4C)alkylsulfonyloxy, an alkali metal phosphato group, or a group of the formula:

wherein $R^8$ and $R^9$ each independently represent hydrogen, hydroxy or (1-4C)alkoxy,
and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy substituents;
provided that when $Q^1$ represents hydrogen or methoxy and $Q^4$ represents hydrogen, then $Q^2$ and $Q^3$ do not both represent methoxy.

In the second aspect of the present invention, $Q^1$, $Q^2$, $Q^3$ and $Q^4$ may each independently represent hydrogen, hydroxy, nitro, thiol, (1-4C)alkoxy, amino, (1-4C)alkylsulfonyloxy or an alkali metal phosphato group, or
any one of $Q^2$ and $Q^3$ or $Q^3$ and $Q^4$ (especially $Q^2$ and $Q^3$) may represent a methylenedioxy group;
and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy (especially halogeno, such as fluoro) substituents;
provided that when $Q^1$ represents hydrogen or methoxy and $Q^4$ represents hydrogen, then $Q^2$ and $Q^3$ do not both represent methoxy.

In the second aspect of the present invention, $Q^1$, $Q^2$, $Q^3$ and $Q^4$ may each independently represent hydrogen, hydroxy, nitro, thiol, (1-4C)alkoxy, amino, (1-4C)alkylsulfonyloxy or an alkali metal phosphato group,
wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy (especially halogeno, such as fluoro) substituents;
provided that when $Q^1$ represents hydrogen or methoxy and $Q^4$ represents hydrogen, then $Q^2$ and $Q^3$ do not both represent methoxy.

In the second aspect of the present invention, $Q^1$, $Q^2$, $Q^3$ and $Q^4$ may each independently represent hydrogen, hydroxy, thiol, (1-4C)alkoxy, amino, (1-4C)alkylsulfonyloxy or an alkali metal phosphato group, and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy (especially halogeno, such as fluoro) substituents;

provided that when $Q^1$ represents hydrogen or methoxy and $Q^4$ represents hydrogen, then $Q^2$ and $Q^3$ do not both represent methoxy.

In the second aspect of the present invention, $Q^1$, $Q^2$, $Q^3$ and $Q^4$ may each independently represent hydrogen, hydroxy, thiol, methoxy, amino, trifluoromethylsulfonyloxy or a disodium phosphato group, provided that when $Q^1$ represents hydrogen or methoxy and $Q^4$ represents hydrogen, then $Q^2$ and $Q^3$ do not both represent methoxy.

In particular, in any aspect of the present invention, $Q^1$ may represent hydrogen.

For example, in the second aspect of the present invention, $Q^1$ may represent hydrogen and $Q^2$, $Q^3$ and $Q^4$ may each independently hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

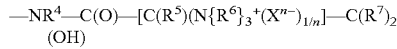
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or any one of $Q^2$ and $Q^3$ or $Q^3$ and $Q^4$ represents a methylenedioxy group;

and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents;

provided that when $Q^4$ represents hydrogen, then $Q^2$ and $Q^3$ do not both represent methoxy.

For example, in the second aspect of the present invention, $Q^1$ may represent hydrogen and $Q^2$, $Q^3$ and $Q^4$ may each independently hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

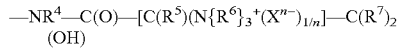
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents;

provided that when $Q^4$ represents hydrogen, then $Q^2$ and $Q^3$ do not both represent methoxy.

For example, in the second aspect of the present invention, $Q^1$ may represent hydrogen and $Q^2$, $Q^3$ and $Q^4$ may each independently represent hydrogen, halogeno, hydroxy, thiol, (2-4C)alkynyl, (1-4C)alkoxy, amino, (1-4C)alkylsulfonyloxy, an alkali metal phosphato group, or a group of the formula:

wherein $R^8$ and $R^9$ each independently represent hydrogen, hydroxy or (1-4C)alkoxy, and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy substituents;

provided that when $Q^4$ represents hydrogen, then $Q^2$ and $Q^3$ do not both represent methoxy.

For example, in the second aspect of the present invention, $Q^1$ may represent hydrogen and $Q^2$, $Q^3$ and $Q^4$ may each independently represent hydrogen, hydroxy, nitro, thiol, (1-4C)alkoxy, amino, (1-4C)alkylsulfonyloxy or an alkali metal phosphato group, or any one of $Q^2$ and $Q^3$ or $Q^3$ and $Q^4$ (especially $Q^2$ and $Q^3$) may represent a methylenedioxy group;

and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy (especially halogeno, such as fluoro) substituents;

provided that when $Q^4$ represents hydrogen, then $Q^2$ and $Q^3$ do not both represent methoxy.

For example, in the second aspect of the present invention, $Q^1$ may represent hydrogen and $Q^2$, $Q^3$ and $Q^4$ may each independently represent hydrogen, hydroxy, nitro, thiol, (1-4C)alkoxy, amino, (1-4C)alkylsulfonyloxy or an alkali metal phosphato group, wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy (especially halogeno, such as fluoro) substituents;

provided that when $Q^4$ represents hydrogen, then $Q^2$ and $Q^3$ do not both represent methoxy.

For example, in the second aspect of the present invention, $Q^1$ may represent hydrogen and $Q^2$, $Q^3$ and $Q^4$ may each independently represent hydrogen, hydroxy, thiol, (1-4C)alkoxy, amino, (1-4C)alkylsulfonyloxy or an alkali metal phosphato group, and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy (especially halogeno, such as fluoro) substituents;

provided that when $Q^4$ represents hydrogen, then $Q^2$ and $Q^3$ do not both represent methoxy.

In any aspect of the present invention, $Q^4$ may represent a group other than hydrogen. In other words, in this embodiment, the group $Q^4$ does not represent hydrogen.

In any aspect of the present invention, preferably at least one of $Q^1$, $Q^2$, $Q^3$ and $Q^4$ is hydrogen and at least one of $Q^1$, $Q^2$, $Q^3$ and $Q^4$ is a group other than hydrogen as defined herein. For example, $Q^1$ may represent hydrogen and at least one of $Q^2$, $Q^3$ and $Q^4$ may represent a group other than hydrogen as defined herein. In particular, $Q^1$ may represent hydrogen and $Q^4$ may represent a group other than hydrogen as defined herein (and $Q^2$ and $Q^3$ may be as defined herein).

Preferably, in any aspect of the present invention, when any of the $Q^1$, $Q^2$, $Q^3$ and/or $Q^4$ substituents represents an (1-4C) alkylsulfonyloxy group, then the $CH_2$ or $CH_3$ groups within the (1-4C)alkyl group bear one or more halogeno or hydroxy (especially halogeno, such as fluoro) substituents. For example, any such $CH_3$ groups within the (1-4C)alkyl group may bear from one to three (especially three) halogeno or hydroxy (especially halogeno, such as fluoro) substituents. Thus, a suitable such substituent may be trifluoromethylsulfonyloxy.

In any aspect of the present invention, $R^1$, $R^2$ and $R^3$ may each independently represent (1-2C)alkoxy (especially methoxy), wherein any $CH_2$ or $CH_3$ group within a $R^1$, $R^2$ and/or $R^3$ substituent optionally bears on each said $CH_2$ or $CH_3$ group one or more halogeno or hydroxy substituents.

In any aspect of the present invention, $R^1$, $R^2$ and $R^3$ may all be the same and may represent (1-2C)alkoxy (especially methoxy), wherein any $CH_2$ or $CH_3$ group within a $R^1$, $R^2$ and/or $R^3$ substituent optionally bears on each said $CH_2$ or $CH_3$ group one or more halogeno or hydroxy substituents.

In any aspect of the present invention, $R^1$, $R^2$ and $R^3$ may all be the same and may represent (1-2C)alkoxy, particularly methoxy.

In any aspect of the present invention, $R^1$, $R^2$ and $R^3$ each independently represent (1-2C)alkoxy. More particularly, $R^1$, $R^2$ and $R^3$ may each represent methoxy.

In particular, in any aspect of the present invention, $Q^1$ may represent hydrogen and at least one, preferably at least two, of the groups $Q^2$, $Q^3$ and $Q^4$ may represent a group other than hydrogen as defined above. For example, in any aspect of the present invention, $Q^1$ may represent hydrogen, $Q^4$ may represent a group other than hydrogen as defined above and at least one of the groups $Q^2$ and $Q^3$ may represent a group other than hydrogen as defined above. Thus, preferred compounds of the Formula I, for example as defined in relation to the second aspect of the present invention, are as follows:

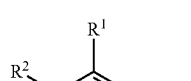

I'

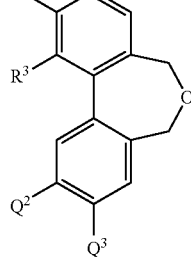

I''

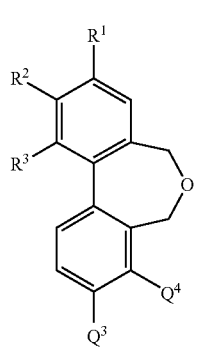

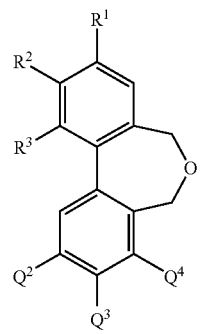

I'''

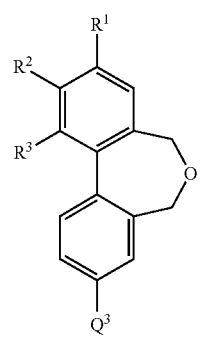

I'''' wherein $R^1$, $R^2$ and $R^3$ are as defined above and $Q^2$, $Q^3$ and $Q^4$, when present, are as defined above except that they do not represent hydrogen. As the skilled person would appreciate, in the compounds of the Formula I' above, the groups represented by $Q^1$ and $Q^4$ in the compounds of the Formula I are hydrogen. Similarly, in the compounds of the Formula I'' above, the groups represented by $Q^1$ and $Q^2$ in the compounds of the Formula I are hydrogen, in the compounds of the Formula I''' above, the group represented by $Q^1$ in the compounds of the Formula I is hydrogen and in the compounds of the Formula I'''' above, the groups represented by $Q^1$, $Q^2$ and $Q^4$ in the compounds of the Formula I are hydrogen.

In particular, there is provided a compound of the Formula I':

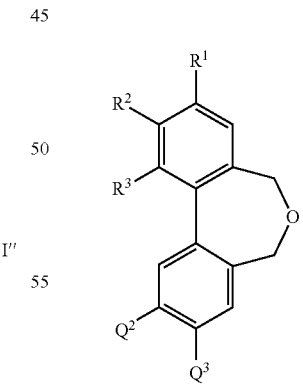

I' or a pharmaceutically acceptable salt thereof wherein:

$R^1$, $R^2$ and $R^3$ each independently represent (1-4C)alkoxy (such as (1-2C)alkoxy, especially methoxy);

$Q^2$ and $Q^3$ each independently represent halogeno, hydroxy, cyano, nitro, trifluoromethyl, thiol, (1-4C)alkyl, (2-4C)alkenyl, (2-4C)alkynyl, (1-4C)alkoxy, amino, (1-4C)

alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

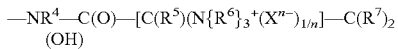
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or $Q^3$ and $Q^4$ represent a methylenedioxy group;

and wherein any $CH_2$ or $CH_3$ group within a $R^1$, $R^2$, $R^3$, $Q^3$ and/or $Q^4$ substituent optionally bears on each said $CH_2$ or $CH_3$ group one or more halogeno or hydroxy substituents;

provided that $Q^2$ and $Q^3$ do not both represent methoxy.

In the compound of the Formula I', or a pharmaceutically acceptable salt thereof, $Q^2$ and $Q^3$ preferably do not each independently represent (1-4C)alkoxy.

In the compound of the Formula I', or a pharmaceutically acceptable salt thereof, $Q^2$ and $Q^3$ may each independently represent halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, an alkali metal phosphato group, or a group of the formula:

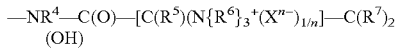
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or $Q^3$ and $Q^4$ may represent a methylenedioxy group;

and wherein any $CH_2$ or $CH_3$ group within a $R^1$, $R^2$, $R^3$, $Q^2$ and/or $Q^3$ substituent optionally bears on each said $CH_2$ or $CH_3$ group one or more halogeno or hydroxy substituents;

provided that $Q^2$ and $Q^3$ do not both represent methoxy.

In the compound of the Formula I', or a pharmaceutically acceptable salt thereof, $Q^2$ and $Q^3$ may each independently represent halogeno, hydroxy, cyano, nitro, trifluoromethyl, thiol, (1-4C)alkyl, (2-4C)alkenyl, (2-4C)alkynyl, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

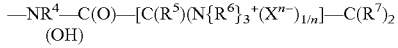
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or $Q^3$ and $Q^4$ may represent a methylenedioxy group;

and wherein any $CH_2$ or $CH_3$ group within a $R^1$, $R^2$, $R^3$, $Q^3$ and/or $Q^4$ substituent optionally bears on each said $CH_2$ or $CH_3$ group one or more halogeno or hydroxy substituents.

In particular in the compound of the Formula I', or a pharmaceutically acceptable salt thereof, $Q^2$ and $Q^3$ may represent a methylenedioxy group.

In particular, there is provided a compound of the Formula I":

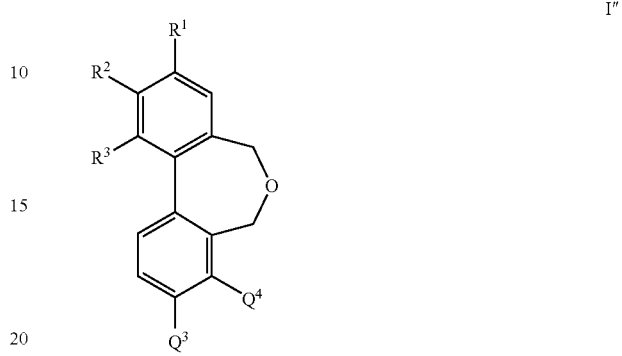

or a pharmaceutically acceptable salt thereof
wherein:
$R^1$, $R^2$ and $R^3$ each independently represent (1-4C)alkoxy (such as (1-2C)alkoxy, especially methoxy);

$Q^3$ and $Q^4$ each independently represent halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

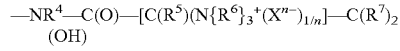
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or $Q^3$ and $Q^4$ may represent a methylenedioxy group;

and wherein any $CH_2$ or $CH_3$ group within a $R^1$, $R^2$, $R^3$, $Q^3$ and/or $Q^4$ substituent optionally bears on each said $CH_2$ or $CH_3$ group one or more halogeno or hydroxy substituents.

In the compound of the Formula I", or a pharmaceutically acceptable salt thereof, $Q^3$ and $Q^4$ may each independently represent halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

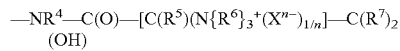
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, and wherein any $CH_2$ or $CH_3$ group within a $R^1$, $R^2$, $R^3$, $Q^3$ and/or $Q^4$ substituent optionally bears on each said $CH_2$ or $CH_3$ group one or more halogeno or hydroxy substituents.

In the compound of the Formula I", or a pharmaceutically acceptable salt thereof, $Q^3$ and $Q^4$ may each independently represent halogeno, hydroxy, thiol, (2-4C)alkynyl, (1-4C)alkoxy, amino, (1-4C)alkylsulfonyloxy, an alkali metal phosphato group, or a group of the formula:

—BR$^8$R$^9$ wherein R$^8$ and R$^9$ each independently represent hydrogen, hydroxy or (1-4C)alkoxy, and wherein any CH$_2$ or CH$_3$ group within a $Q^3$ and/or $Q^4$ substituent optionally bears on each said CH$_2$ or CH$_3$ group one or more halogeno or hydroxy substituents.

In the compound of the Formula I", or a pharmaceutically acceptable salt thereof, $Q^3$ and $Q^4$ may each independently represent hydroxy, thiol, (1-4C)alkoxy, amino, (1-4C)alkylsulfonyloxy or an alkali metal phosphato group, wherein any CH$_2$ or CH$_3$ group within a $Q^3$ and/or $Q^4$ substituent optionally bears on each said CH$_2$ or CH$_3$ group one or more halogeno or hydroxy substituents.

Further, in the compound of the Formula I", or a pharmaceutically acceptable salt thereof, $Q^3$ may represent (1-4C)alkoxy (such as (1-2C)alkoxy, such as methoxy) and $Q^4$ may represent hydroxy, thiol, amino, (1-4C)alkylsulfonyloxy or an alkali metal phosphato group, wherein any CH$_2$ or CH$_3$ group within a $Q^3$ and/or $Q^4$ substituent optionally bears on each said CH$_2$ or CH$_3$ group one or more halogeno or hydroxy substituents.

Further in the compound of the Formula I", or a pharmaceutically acceptable salt thereof, $Q^3$ and $Q^4$ may each independently represent hydroxy, thiol, (1-4C)alkoxy, amino, (1-4C)alkylsulfonyloxy or an alkali metal phosphato group, wherein any CH$_2$ or CH$_3$ group within a $Q^3$ and/or $Q^4$ substituent optionally bears on each said CH$_2$ or CH$_3$ group one or more halogeno or hydroxy (especially halogeno, such as fluoro) substituents. In particular, $Q^3$ may represent (1-4C)alkoxy (such as (1-2C)alkoxy, for example methoxy) and $Q^4$ may represent hydroxy, thiol, amino, (1-4C)alkylsulfonyloxy or an alkali metal phosphato group, wherein any CH$_2$ or CH$_3$ group within a $Q^3$ and/or $Q^4$ substituent optionally bears on each said CH$_2$ or CH$_3$ group one or more halogeno or hydroxy (especially halogeno, such as fluoro) substituents.

Further in the compound of the Formula I", or a pharmaceutically acceptable salt thereof, $Q^3$ and $Q^4$ may each independently represent hydroxy, thiol, methoxy, amino, trifluoromethylsulfonyloxy or a disodium phosphato group. In particular, $Q^3$ may represent methoxy and $Q^4$ represent hydroxy, thiol, amino, trifluoromethylsulfonyloxy or a disodium phosphato group.

In particular, there is provided a compound of the Formula I"':

I"' or a pharmaceutically acceptable salt thereof wherein:

R$^1$, R$^2$ and R$^3$ each independently represent (1-4C)alkoxy (such as (1-2C)alkoxy, for example methoxy);

$Q^2$, $Q^3$ and $Q^4$ each independently represent halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

—NR$^4$—C(O)—[C(R$^5$)(N{R$^6$}$_3^+$(X$^{n-}$)$_{1/n}$]—C(R$^7$)$_2$
(OH)

wherein R$^4$, R$^5$, R$^6$ and R$^7$ each independently represent hydrogen, (1-4C)alkyl, (2-4C)alkenyl or (2-4C)alkynyl, X$^{n-}$ represents a suitable anion and n is 1 or 2, or a group of the formula:

—BR$^8$R$^9$ wherein R$^8$ and R$^9$ each independently represent hydrogen, hydroxy or (1-4C)alkoxy, or any one of $Q^2$ and $Q^3$ or $Q^3$ and $Q^4$ represents a methylenedioxy group;

and wherein any CH$_2$ or CH$_3$ group within a R$^1$, R$^2$, R$^3$, $Q^2$, $Q^3$ and/or $Q^4$ substituent optionally bears on each said CH$_2$ or CH$_3$ group one or more halogeno or hydroxy substituents.

In the compound of the Formula I"', or a pharmaceutically acceptable salt thereof, $Q^2$, $Q^3$ and $Q^4$ may each independently represent halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

—NR$^4$—C(O)—[C(R$^5$)(N{R$^6$}$_3^+$(X$^{n-}$)$_{1/n}$]—C(R$^7$)$_2$
(OH)

wherein R$^4$, R$^5$, R$^6$ and R$^7$ each independently represent hydrogen, (1-4C)alkyl, (2-4C)alkenyl or (2-4C)alkynyl, X$^{n-}$ represents a suitable anion and n is 1 or 2, or a group of the formula:

—BR$^8$R$^9$ wherein R$^8$ and R$^9$ each independently represent hydrogen, hydroxy or (1-4C)alkoxy, and wherein any CH$_2$ or CH$_3$ group within a R$^1$, R$^2$, R$^3$, $Q^2$, $Q^3$ and/or $Q^4$ substituent optionally bears on each said CH$_2$ or CH$_3$ group one or more halogeno or hydroxy substituents.

In the compound of the Formula I"', or a pharmaceutically acceptable salt thereof, $Q^2$, $Q^3$ and $Q^4$ may each independently represent halogeno, hydroxy, thiol, (2-4C)alkynyl, (1-4C)alkoxy, amino, (1-4C)alkylsulfonyloxy, an alkali metal phosphato group, or a group of the formula:

—BR$^8$R$^9$ wherein R$^8$ and R$^9$ each independently represent hydrogen, hydroxy or (1-4C)alkoxy, and wherein any CH$_2$ or CH$_3$ group within a $Q^2$, $Q^3$ and/or $Q^4$ substituent optionally bears on each said CH$_2$ or CH$_3$ group one or more halogeno or hydroxy substituents.

In the compound of the Formula I"', or a pharmaceutically acceptable salt thereof, $Q^2$, $Q^3$ and $Q^4$ may each independently represent hydroxy, thiol, (1-4C)alkoxy, amino, (1-4C)alkylsulfonyloxy or an alkali metal phosphato group, wherein any CH$_2$ or CH$_3$ group within a $Q^2$, $Q^3$ and/or $Q^4$ substituent optionally bears on each said CH$_2$ or CH$_3$ group one or more halogeno or hydroxy substituents.

In particular, there is provided a compound of the Formula I'''':

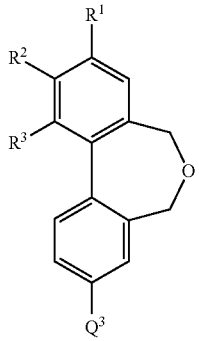

I'''' or a pharmaceutically acceptable salt thereof
wherein:

R¹, R² and R³ each independently represent (1-4C)alkoxy (such as (1-2C)alkoxy, for example methoxy);

Q³ represents halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

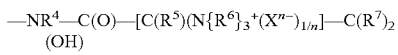

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, and wherein any $CH_2$ or $CH_3$ group within a R¹, R², R³ and/or Q³ substituent optionally bears on each said $CH_2$ or $CH_3$ group one or more halogeno or hydroxy substituents.

In the compound of the Formula I'''', or a pharmaceutically acceptable salt thereof, Q³ may represent nitro, (1-4C)alkoxy, amino, (1-4C)alkylamino or di-[(1-4C)alkyl]amino, more particularly (1-4C)alkoxy, amino, (1-4C)alkylamino or di-[(1-4C)alkyl]amino, even more particularly (1-4C)alkoxy.

In the compounds of the Formula I', I'', I''' or I'''', or a pharmaceutically acceptable salt thereof, as defined above, R¹, R² and R³ may particularly each independently represent (1-2C)alkoxy, more particularly, R¹, R² and R³ may each represent methoxy.

A particular group of compounds of the Formula I according to any aspect of the present invention may have the Formula IA (where "Me" represents methyl):

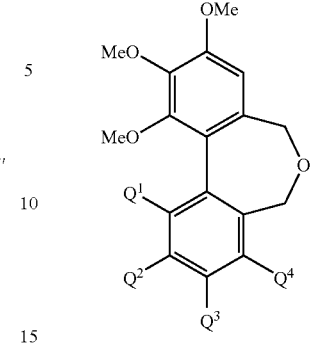

IA wherein Q¹, Q², Q³ and Q⁴ are as defined above, or a pharmaceutically acceptable salt thereof.

A further particular group of compounds of the Formula I according to any aspect of the present invention may have the Formula IB (where "Me" represents methyl):

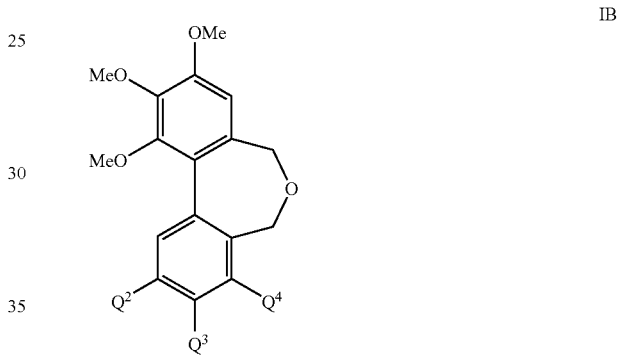

IB wherein Q², Q³ and Q⁴ are as defined above, or a pharmaceutically acceptable salt thereof. As the skilled person would appreciate, in the compounds of the Formula IB above, the group represented by Q¹ in the compounds of the Formula I is hydrogen.

Particular compounds of the present invention are, for example, one or more compounds of the Formula I selected from:

1,2,3,9-tetramethoxy-5,7-dihydrodibenzo[c,e]oxepine;
5,7-dihydro-1,2,3-trimethoxybenzo[d][1,3]dioxolo[4,5-h][2]benzoxepin; and
3,9,10,11-tetramethoxy-5,7-dihydrodibenzo[c,e]oxepin-4-ol;

or a pharmaceutically acceptable salt thereof

Further particular compounds of the present invention are, for example, one or more compounds of the Formula I selected from:

3,9,10,11-tetramethoxy-5,7-dihydrodibenzo[c,e]oxepin-4-yl disodium phosphate;
1,2,3-trimethoxy-9-nitro-5,7-dihydrodibenzo[c,e]oxepine;
9,10,11-trimethoxy-5,7-dihydrodibenzo[c,e]oxepin-3-amine;
3,9,10,11-tetramethoxy-5,7-dihydrodibenzo[c,e]oxepin-4-yl trifluoromethanesulfonate;
3,9,10,11-tetramethoxy-5,7-dihydrodibenzo[c,e]oxepine-4-thiol; and
3,9,10,11-tetramethoxy-5,7-dihydrodibenzo[c,e]oxepin-4-amine;

or a pharmaceutically acceptable salt thereof.

A further particular compound of the present invention is, for example, a compound of the Formula I' selected from:

5,7-dihydro-1,2,3-trimethoxybenzo[d][1,3]dioxolo[4,5-h][2]benzoxepin;

or a pharmaceutically acceptable salt thereof.

Further particular compounds of the present invention are, for example, one or more compounds of the Formula I" selected from:

3,9,10,11-tetramethoxy-5,7-dihydrodibenzo[c,e]oxepin-4-ol;

3,9,10,11-tetramethoxy-5,7-dihydrodibenzo[c,e]oxepin-4-yl disodium phosphate;

3,9,10,11-tetramethoxy-5,7-dihydrodibenzo[c,e]oxepin-4-yl trifluoromethanesulfonate;

3,9,10,11-tetramethoxy-5,7-dihydrodibenzo[c,e]oxepine-4-thiol; and 3,9,10,11-tetramethoxy-5,7-dihydrodibenzo[c,e]oxepin-4-amine;

or a pharmaceutically acceptable salt thereof

Further particular compounds of the present invention are, for example, one or more compounds of the Formula I"" selected from:

1,2,3,9-tetramethoxy-5,7-dihydrodibenzo[c,e]oxepine;

1,2,3-trimethoxy-9-nitro-5,7-dihydrodibenzo[c,e]oxepine; and 9,10,11-trimethoxy-5,7-dihydrodibenzo[c,e]oxepin-3-amine;

or a pharmaceutically acceptable salt thereof.

A compound of the Formula I, or a pharmaceutically acceptable salt thereof, may be prepared by any process known to be applicable to the preparation of chemically-related compounds. The present invention provides such processes, when used to prepare a compound of the Formula I, which processes are illustrated by the following representative process variants in which, unless otherwise stated, $R^1$, $R^2$, $R^3$, $Q^1$, $Q^2$, $Q^3$ and $Q^4$ have any of the meanings defined herein. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated, which are within the ordinary skill of an organic chemist.

For example, a compound of the Formula I, or a pharmaceutically acceptable salt thereof, may be prepared by the reaction of a compound of the Formula II:

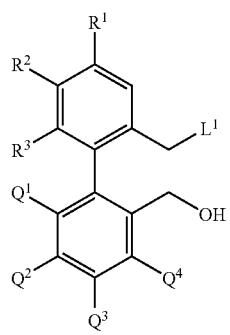

II wherein $R^1$, $R^2$, $R^3$, $Q^1$, $Q^2$, $Q^3$ and $Q^4$ have any of the meanings defined herein except that any functional group is protected if necessary and $L^1$ is a suitable displaceable group such as a halogeno (for example chloro, bromo or iodo, especially bromo), a carboxylate, a para-toluenesulfonate or a hydroxy group, with a suitable ring closure reagent; and optionally, (i) converting a compound of the Formula I into another compound of the Formula I; and/or (ii) removing any protecting group that is present (by conventional means); and/or (iii) forming a pharmaceutically acceptable salt.

As the skilled person would appreciate, in the reaction of a compound of the Formula II any suitable ring closure reagent may be used and the particular reagent selected will depend on the nature of the displaceable group, $L^1$.

When $L^1$ is a hydroxy group, the ring closure is conveniently carried out under suitable acid-catalysed dehydration conditions. Suitable acids for the dehydration reaction include mineral acids, such as hydrochloric acid, sulfuric acid, trifluoroacetic acid and para-toluenesulfonic acid. The acid-catalysed dehydration reaction is conveniently carried out in the presence of a suitable inert solvent or diluent, for example an ether such as tetrahydrofuran, 1,4-dioxane or 1,2-dimethoxyethane. The acid-catalysed dehydration reaction is conveniently carried out at a temperature in the range, for example, from ambient to 200° C., conveniently at or near the reflux temperature of the solvent. Further details of the conditions suitable for conducting acid-catalysed dehydration reactions can be found in Insole, J. M., 1990, J. Chem. Res. (S), 378-379, (M) 2831-2867.

When $L^1$ is a halogeno group (especially bromo), the ring closure is conveniently carried out under suitable conditions for an intramolecular Williamson reaction. The intramolecular Williamson reaction is conveniently carried out by reaction of the compound of the Formula II with a suitable base. Suitable bases include the alkali or alkaline earth metal hydroxides, tert-butoxides and carbonates, such as sodium hydroxide and potassium carbonate. The intramolecular Williamson reaction is conveniently carried out in the presence of a suitable inert solvent or diluent, for example a polar solvent such as dimethylsulfoxide. Further details of the conditions suitable for conducting intramolecular Williamson reactions can be found in a review of the Williamson ether synthesis in Feuer, H.; Hooz, J., The Chemistry of the Ether Linkage, ed. Patai, S., Wiley, New York, 1967, 446-460.

The conversion of a compound of the Formula I into another compound of the Formula I may be carried out using standard procedures of organic chemistry. Examples of the types of conversion reactions that may be used include the introduction of a substituent by means of an electrophilic aromatic substitution reaction, an intramolecular (rearrangement) reaction (for example a Fries reaction or an aromatic Claisen rearrangement reaction), an aromatic radical or nucleophilic substitution reaction, the reduction of substituents, the alkylation of substituents and the oxidation of substituents. In particular, conversion reactions that may be carried out include nitration reactions, Friedel-Crafts acylation reactions and phenol oxidation reactions. The reagents and reaction conditions for such conversion reactions are well known in the chemical art.

Compounds of the Formula II may be obtained by standard procedures of organic chemistry, for example using known processes described in the literature.

For example, compounds of the Formula II wherein $L^1$ represents a hydroxy group may be obtained by standard procedures of organic chemistry, as shown in Reaction Scheme 1:

Reaction Scheme 1

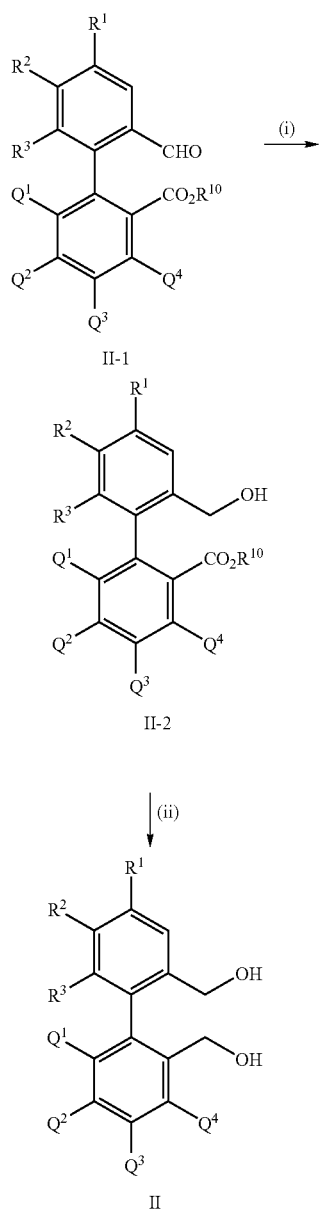

wherein $R^1$, $R^2$, $R^3$, $Q^1$, $Q^2$, $Q^1$ and $Q^4$ have any of the meanings defined herein except that any functional group is protected if necessary and $R^{10}$ represents hydrogen or a (1-4C)alkyl group.

As the skilled person would appreciate, in step (i) of Reaction Scheme 1, an aldehyde group is reduced to an alcohol group. This reduction may be conducted using any suitable reducing agent for the reduction of an aldehyde. In Reaction Scheme 1, the reducing agent selected for step (i) is a suitable reducing agent for the reduction of an aldehyde but is not also suitable for the reduction of an ester group (see step (ii) of Reaction Scheme 1). For example, the reduction of the aldehyde group in step (i) of Reaction Scheme 1 may be carried out using sodium borohydride as the reducing agent, in the presence of a suitable inert solvent or diluent, for example an alcohol such as methanol or ethanol, an ether such as tetrahydrofuran, 1,4-dioxane or 1,2-dimethoxyethane or an aromatic solvent such as toluene, and at a temperature in the range, for example, from 0° C. to ambient.

As the skilled person would appreciate, in step (ii) of Reaction Scheme 1, a carboxylic acid or ester group is reduced to an alcohol group. This reduction may be conducted using any suitable reducing agent for the reduction of a carboxylic acid or ester. For example, the reduction of the carboxylic acid or ester group in step (ii) of Reaction Scheme 1 may be carried out using lithium borohydride, lithium aluminumhydride or sodium bis(2-methoxyethoxy)aluminumhydride (Red-Al) as the reducing agent, in the presence of a suitable inert solvent or diluent, for example an ether such as diethyl ether, tetrahydrofuran, 1,4-dioxane or 1,2-dimethoxyethane or an aromatic solvent such as toluene, and at a temperature in the range, for example, from ambient to 150° C., conveniently at or near the reflux temperature of the solvent.

As the skilled person would appreciate, the compound of the Formula II-1 may be converted directly to a compound of the Formula II in one direct process step by selecting a reducing agent that is capable of reducing both an aldehyde group and a carboxylic acid or ester group to an alcohol group. This reduction may be conducted using a reducing agent and reaction conditions as discussed above for step (ii) of Reaction Scheme 1.

The compounds of the Formula II wherein $L^1$ represents a hydroxy group may be obtained by the route as shown in Reaction Scheme 2:

Reaction Scheme 2

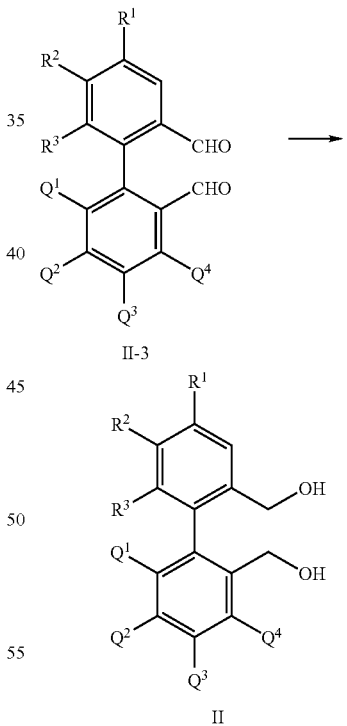

wherein $R^1$, $R^2$, $R^3$, $Q^1$, $Q^2$, $Q^3$ and $Q^4$ have any of the meanings defined herein except that any functional group is protected if necessary.

As the skilled person would appreciate, in Reaction Scheme 2, both aldehyde groups are reduced to alcohol groups at the same time. This reduction may be conducted using the reagents and conditions discussed above in relation to step (i) of Reaction Scheme 1.

The aldehyde groups of the compound of the Formula II-3 in Reaction Scheme 2 may both be replaced by a carboxylic acid or ester group, both of which groups may then be reduced to alcohol groups at the same time. This reduction may be conducted using the reagents and conditions discussed above in relation to step (ii) of Reaction Scheme 1.

Compounds of the Formula II wherein $L^1$ represents a halogeno group may be obtained by standard procedures of organic chemistry, for example from compounds of the Formula II wherein $L^1$ represents a hydroxy group. Suitable reaction conditions for such a conversion reaction are described in, for example, Corey, E. J., Kim, C. U. and Takeda, M., Tetrahedron Lett., 1972, 4339-4342 and Munyemana, F., Frisque-Hesbain, A. M., Devos, A. and Ghosez, L., Tetrahedron Lett., 1989, 30, 3077-3080.

Compounds of the Formula II wherein $L^1$ represents a halogeno group may be obtained by a route as shown in Reaction Scheme 3:

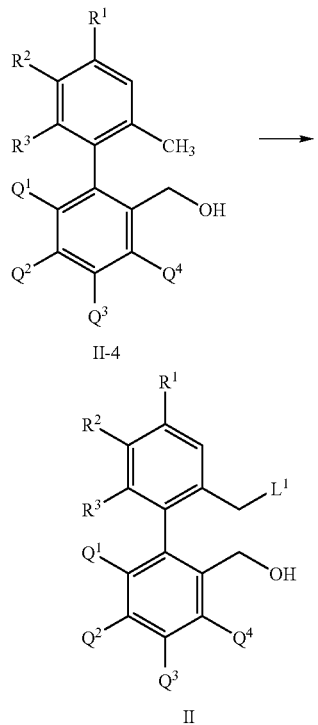

wherein $R^1$, $R^2$, $R^3$, $Q^1$, $Q^2$, $Q^3$ and $Q^4$ have any of the meanings defined herein except that any functional group is protected if necessary.

The reaction shown in Reaction Scheme 3 may conveniently be carried out using a suitable radical reaction, for example by reaction of a compound of the Formula II-4 with an N-halosuccinimide reagent and a radical initiator in the presence of light and/or heat. Further details of the conditions suitable for conducting such a radical reaction can be found in Ghera, E., Plemenitas, A. and Ben-David, Y., Synthesis, 1984, 504.

Compounds of the Formula II-1 above may be obtained by standard procedures of organic chemistry, for example as shown in Reaction Scheme 4:

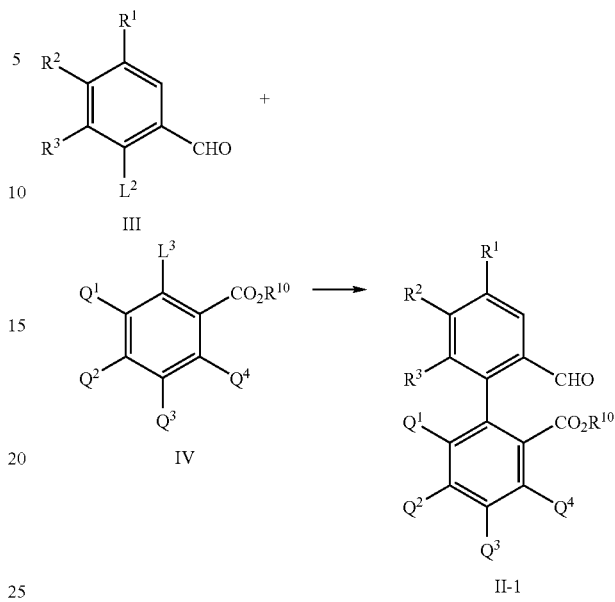

wherein $R^1$, $R^2$, $R^3$, $Q^1$, $Q^2$, $Q^3$ and $Q^4$ have any of the meanings defined herein except that any functional group is protected if necessary, $R^{10}$ represents hydrogen or a (1-4C) alkyl group and $L^2$ and $L^3$ each represent a suitable displaceable group such as a halogeno (for example chloro, bromo or iodo) group.

As the skilled person would appreciate, the reaction of the compounds of the Formulae III and IV in Reaction Scheme 4, may conveniently be carried out under any suitable conditions for a coupling reaction. For example, the reaction may conveniently be carried out under suitable conditions for an Ullmann coupling reaction. Such a reaction is conveniently carried out by reaction of the compounds of the Formulae III and IV in the presence of a copper-bronze alloy. The reaction is conveniently conducted in the absence or presence of a suitable inert solvent or diluent, for example a dipolar aprotic solvent such as N,N-dimethylformamide or N,N-dimethylacetamide and at a temperature in the range, for example, from ambient to 250° C. Further details of the conditions suitable for conducting Ullmann coupling reactions can be found in reviews of the Ullmann and other methods for aryl-aryl coupling, for example in Hassan, J., Sevignon, M., Gozzi, C., Schulz, E., Lemaire, M., Chem. Rev., 2002, 102, 1359-1469 and Nelson, T. D., Crouch, R. D., Org. React., 2004, 63, 265-555.

As the skilled person would appreciate, the reaction of the compounds of the Formulae III and IV in Reaction Scheme 4 may conveniently be carried out under suitable conditions for a Suzuki-Miyaura reaction. Further details of the conditions suitable for conducting Suzuki-Miyaura reactions can be found in reviews of the Suzuki-Miyaura reaction, for example in Miyaura, N. and Suzuki, A., Chem. Rev., 1995, 95, 2457-2483 and Suzuki, A., J. Organometallic Chem., 1999, 576, 147-168.

Compounds of the Formulae II-2, II-3 and II-4 above may be obtained by standard procedures of organic chemistry, for example by analogous reactions to that described in Reaction Scheme 4 above.

The compounds of the Formulae III and IV are commercially available or may be prepared using conventional procedures of organic chemistry, which would be well known to a person skilled in the art.

As the skilled person would appreciate, the preparation of compounds of the Formula I may involve, at various stages, the addition and removal of one or more protecting groups. The protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule. The protection and deprotection of functional groups is described in 'Protective Groups in Organic Synthesis', 2nd edition, T. W. Greene and P. G. M. Wuts, Wiley-Interscience (1991). For example, a suitable hydroxy protecting group may be a methanesulfonate group.

As the skilled person would appreciate, by the term "inert solvent or diluent" we mean a solvent or diluent that does not react with the starting materials, reagents, intermediates or products in a manner which adversely affects the yield of the desired product.

As a person skilled in the art would appreciate, in order to obtain compounds of the present invention in an alternative and possibly more convenient manner, the individual process steps mentioned hereinbefore may be performed in a different order and/or the individual reactions may be performed at different stage in the overall route.

As discussed above, some of the compounds according to the present invention may exist as stereoisomers. Stereoisomers may be separated using conventional techniques, for example chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free from other stereoisomers, for example containing less than 20%, particularly less than 10% and more particularly less than 5% by weight of other stereoisomers.

Certain intermediates used in the processes described above are novel and form a further feature of the present invention. Accordingly there is provided a compound selected from a compound the Formulae II, II-1, II-2, II-3 and II-4 as herein defined, or a salt thereof. The intermediate may be in the form of a salt of the intermediate. Such salts need not be pharmaceutically acceptable salts. For example it may be useful to prepare an intermediate in the form of a pharmaceutically non-acceptable salt if, for example, such salts are useful in the manufacture of a compound of the Formula I.

The activities of the compounds of the present invention as vascular targeting agents were assessed in biological assays, as described below.

Test (a):

The compounds of the present invention were tested in test (a) for growth inhibitory activity ($IC_{50}$) against the K562 human chronic myelogenous leukaemia cell line using a MTT assay generally as described in Tada, H., Shiho, O., Kuroshima, K., Koyama, M., Tsukamoto, K., J. Immunol. Methods 1986, 93, 157 and Edmondson, J. M., Armstrong, L. S., Martinez, A. O., J. Tissue Culture Methods 1988, 11, 15. Cells were cultured in Roswell Park Memorial Institute (RPMI) medium, free of antibiotics and containing L-glutamine (2 μM), supplemented with 10% foetal calf serum. A single suspension of the K562 cell line was tested from an exponentially growing culture. The cells were counted using a haemocytometer, and diluted to $5 \times 10^3$/ml.

A compound of the present invention was dissolved in dimethylsulfoxide (DMSO) at a concentration of 50 μM and 4 μl of the DMSO solution was added to the cell suspension (4 ml). 1 ml of this solution was added to a further 1 ml of cell solution in a neighbouring tube, giving a compound half that of the initial dilution. The dilutions were continued in the same manner affording seven samples at different concentrations. One cell solution was left compound free as a control. Treated cells (200 μl) were pipetted in triplicate into a 96-well plate and incubated at 37° C. in a 5% $CO_2$ in air atmosphere for 5 days. After this time, the plate was removed from the incubator and a solution of (3-(4,5-dimethylthiazol-2-yl)-2, 5-diphenyltetrazolium bromide (MTT) (50 μl, 3 mg/ml in phosphate buffered saline (PBS)) was added to each well. After a further 3 hour incubation period under the same conditions, the medium was carefully removed from each well by suction and the resulting formazan precipitate was dissolved in DMSO (200 μl). The optical density of each well was then read (540 nm) using a Titretek Multiscan MCC/340 platereader. After processing and analysis through the application of an 'in-house' software package, the results obtained enabled the calculation of the drug dose required to inhibit cellular growth by 50% ($GI_{50}$ or $IC_{50}$ value).

Test (b):

The compounds of the present invention were also tested in assay (b) for their ability to inhibit tubulin assembly generally as described in McGown and Fox, "Structural and biochemical comparison of the anti-mitotic agents colchicine, combretastatin A-4 and amphethinile" Anti-Cancer Drug Design, 3, 249, 1989.

Samples were prepared in quartz cuvettes at 0° C. and contained 2-morpholinoethanesulfonic acid (MES) buffer (740 μl, 0.1 M MES, 1 mM ethylene glycol tetraacetic acid (EGTA), 0.5 mM $MgCl_2$, pH 6.6), a compound of the present invention (10 μl, 1 mM in DMSO), tubulin (150 μl, 1/4 dilution of neat tubulin in MES buffer) and GTP (100 μl, 10 mM). The overall concentration of the compound in solution was therefore 10 μM. The cell was mixed well, dried and immediately placed in a Varian Cary 1 UV/Visible spectrophotometer, preheated to 37° C., along with a control sample containing MES buffer (740 μl), guanosine triphosphate (GTP) (100 μl, 10 mM), tubulin (150 μl, concentration as before) and DMSO (10 μl). The absorbance at 350 nm was recorded over a period of 20 minutes. The results were compared with the untreated control experiment to assess the relative degree of change in optical density. If assembly was less than 50% of that of the control, the experiment was repeated using decreasing concentrations (from 1 mM) of the compound in order to determine the activity.

Test (c):

The compounds of the present invention were also tested in in vivo functional vasculature studies using the fluorescent DNA-binding compound Hoechst 33342 (H33342)

Twenty-eight mice were used for test (c). The tumours used were colon carcinomas (DLD-1). Once the tumours reached a suitable size, mice were randomised and assigned into 10 groups with one control group and 3 groups for each compound to be tested (referred to as a "drug group"). Mice in a drug group were treated intraperitoneally with a single dose of a compound of the present invention at a dose believed to be the maximum tolerated dose for each compound being tested (the maximum tolerated dose being measured by dosing mice with increasing amounts of compound (normally doubling the previous dose) until it is either fatal or the animal suffers substantial weight loss or has become distressed). The dose for the compound of Example 1 was 60 mg/kg, for the compound of Example 2 was 120 mg/kg and for the compound of Example 3 was 270 mg/kg. The control group was untreated. H33342 was then injected intravenously at 40 mg/kg to the treated mice 4, 8 and 24 hours after administration of a compound of the present invention and after 24 hours to the untreated control mice. After one minute, each mouse was killed by cervical dislocation and the tumours were removed. Following this procedure the H33342 is confined to the nuclei of cells adjacent to the blood vessels. The tumours were wrapped in aluminium foil and immediately snap-frozen in liquid nitrogen and then stored at −80° C. until required for sectioning. For assessment of tumour vasculature, 10 μm-thick sections were cut using a cryostat (Leica, CM 1100, Scientific Laboratory Supplies, UK) with intervals between sections of 200 μm. The sections were placed on glass slides and allowed to air dry before viewing under a light microscope using UV illumination. Functional vascular volume was quantified using a point scoring system as described previously (Cowen S. E., Bibby M. C., Double J. A., Characterisation of the vasculature within a murine adenocarcinoma growing in different sites to evaluate the potential of vascular therapies, Acta Oncologica, 1995, 34, 357-60). Using a graticule with 22×16 grids, points crossing areas of fluorescence were counted as positive points. The total number of positive points was used to calculate the percentage of functional vasculature. Five sections per tumour and 5 fields per section were examined for tumours.

The results of test (c) are shown in FIG. 1, which is a graph showing relative percentage of control functional vasculature in the DLD-1 tumours after treatment with the compounds of Examples 1, 2 and 3 at doses of 60, 120 and 270 mg/kg respectively. Each point plotted in the graph of FIG. 1 represents the mean percentage of control functional vasculature for each time-point.

The percentage of functional vasculature of the DLD-1 tumour in the control group was 9.22±2.93 (n=2 tumours).

Following administration of the compound of Example 1 at a single dose of 60 mg/kg, functional vasculature in DLD-1 tumours decreased gradually post-treatment and significant decrease were observed at both 8 and 24 hours post-treatment compared to control tumours.

Following administration of the compound of Example 2 at a single dose of 120 mg/kg, no difference in functional vasculature was seen at 4 and 8 hours post-treatment compared to control tumours at 24 hours. However, a significant functional vasculature decrease was observed in DLD-1 tumours 24 hours post-treatment.

Following administration of the compound of Example 3 at a single dose of 120 mg/kg, functional vasculature dramatically decreased at 4 hours post-treatment. However, this reduced functional vasculature restored back to above control level at 8 hours post-treatment. A particular high functional vasculature was seen for one mouse, which contributed to the restoration. Functional vasculature in the other two mice maintained similar level at those at 4 hours post-treatment. At 24 hours post-treatment, percentage functional vasculature significantly decreased again in these tumours compared to control tumours.

The data shown in FIG. 1 shows that the compounds of the present invention potentially could substantially decrease functional vasculature in DLD-1 tumours after 24 hours post-treatment to about 40% of control.

Although the pharmacological properties of the compounds of the present invention vary with structural changes as expected, in general the activity of the compounds in assay (a) was found to be 100 nM or below and in assay (b) was found to be 10 μM or below (preferably 5 μM or below).

By way of example only, the following table illustrates the activity of representative compounds of the present invention:

| Example Number | $IC_{50}$ (nm) - Assay (a)* | $IC_{50}$ (μm)- Assay (b)** |
| --- | --- | --- |
| 1 | 110 | 5.7 |
| 3 | 33.9 | 0.8 |
| 4 | 0.23 | 0.7 |
| 9 | 2.0 | 0.9 |

*concentration to inhibit 50% cell proliferation
**concentration for 50% inhibition of tubulin assembly As discussed above, it is believed that the compounds of the Formula I possess good in vivo activity as vascular targeting agents and for producing a vascular damaging effect. Thus, the compounds of the Formula I are expected to be useful in the treatment of diseases or medical conditions in which the damage or destruction of the vasculature in a warm-blooded animal (such as man) has an effect. For example, it is believed that the compounds of the present invention may be useful in the treatment of cancers, macular degeneration, proliferative retinopathy (such as proliferative diabetic retinopathy), psoriasis and endometriosis, especially cancers, macular degeneration and proliferative retinopathy (such as proliferative diabetic retinopathy), more especially cancers and macular degeneration.

Accordingly, the present invention provides a compound of the Formula I, or a pharmaceutically acceptable salt thereof, as herein defined for use as a medicament. For example, the present invention may provide a compound of the Formula I as defined in respect to the second aspect (including the preferred compound(s) of the Formula I', I'', I''' and/or I''''), or a pharmaceutically acceptable salt thereof, for use as a medicament.

The present invention also provides a compound of the Formula I, or a pharmaceutically acceptable salt thereof, as herein defined for use as a vascular targeting agent in a warm-blooded animal (such as man). For example, the present invention may provide a compound of the Formula I as defined in respect to the second aspect (including the preferred compound(s) of the Formula I', I'', I''' and/or I''''), or a pharmaceutically acceptable thereof, for use as a vascular targeting agent in a warm-blooded animal (such as man).

The present invention further provides the use of a compound of the Formula I, or a pharmaceutically acceptable salt thereof, as herein defined in the manufacture of a medicament for use in the production of a vascular damaging effect in a warm-blooded animal (such as man). For example, the present invention may provide a compound of the Formula I as defined in respect to the second aspect (including the preferred compound(s) of the Formula I', I'', I''' and/or I''''), in the manufacture of a medicament for use in the production of a vascular damaging effect in a warm-blooded animal (such as man).

The present invention provides a method for producing a vascular damaging effect in a warm-blooded animal (such as man) in need of such treatment which comprises administering to said animal an effective amount of a compound of the Formula I, or a pharmaceutically acceptable salt thereof, as herein defined. For example, the present invention may provide a method for producing a vascular damaging effect in a warm-blooded animal (such as man) in need of such treatment which comprises administering to said animal an effective amount of a compound of the Formula I as defined in respect to the second aspect (including the preferred compound(s) of the Formula I', I", I''' and/or I''''), or a pharmaceutically acceptable thereof.

The present invention further provides a compound of the Formula I, or a pharmaceutically acceptable salt thereof, as herein defined for use in the production of a vascular damaging effect in a warm-blooded animal (such as man). For example, the present invention may provide a compound of the Formula I as defined in respect to the second aspect (including the preferred compound(s) of the Formula I', I", I''' and/or I''''), or a pharmaceutically acceptable thereof, for use in the production of a vascular damaging effect in a warm-blooded animal (such as man).

The present invention further provides the use of a compound of the Formula I, or a pharmaceutically acceptable salt thereof, as herein defined in the manufacture of a medicament for use in the production of a vascular damaging effect in a warm-blooded animal (such as man) wherein the vascular damaging effect is produced at least in part by inhibition of tubulin assembly into microtubules thereby interfering with cellular tubulin-microtubule equilibrium. For example, the present invention may provide a compound of the Formula I as defined in respect to the second aspect (including the preferred compound(s) of the Formula I', I", I''' and/or I''''), or a pharmaceutically acceptable thereof, in the manufacture of a medicament for use in the production of a vascular damaging effect in a warm-blooded animal (such as man) wherein the vascular damaging effect is produced at least in part by inhibition of tubulin assembly into microtubules thereby interfering with cellular tubulin-microtubule equilibrium.

The present invention provides a method for producing a vascular damaging effect in a warm-blooded animal (such as man) in need of such treatment, wherein the vascular damaging effect is produced at least in part by inhibition of tubulin assembly into microtubules thereby interfering with cellular tubulin-microtubule equilibrium, which comprises administering to said animal an effective amount of a compound of the Formula I, or a pharmaceutically acceptable salt thereof, as herein defined. For example, the present invention may provide a method for producing a vascular damaging effect in a warm-blooded animal (such as man) in need of such treatment, wherein the vascular damaging effect is produced at least in part by inhibition of tubulin assembly into microtubules thereby interfering with cellular tubulin-microtubule equilibrium, which comprises administering to said animal an effective amount of a compound of the Formula I as defined in respect to the second aspect (including the preferred compound(s) of the Formula I', I", I''' and/or I''''), or a pharmaceutically acceptable thereof.

The present invention further provides a compound of the Formula I, or a pharmaceutically acceptable salt thereof, as herein defined for use in the production of a vascular damaging effect in a warm-blooded animal (such as man) wherein the vascular damaging effect is produced at least in part by inhibition of tubulin assembly into microtubules thereby interfering with cellular tubulin-microtubule equilibrium. For example, the present invention may provide a compound of the Formula I as defined in respect to the second aspect (including the preferred compound(s) of the Formula I', I", I''' and/or I''''), or a pharmaceutically acceptable thereof, for use in the production of a vascular damaging effect in a warm-blooded animal (such as man) wherein the vascular damaging effect is produced at least in part by inhibition of tubulin assembly into microtubules thereby interfering with cellular tubulin-microtubule equilibrium.

The present invention further provides the use of a compound of the Formula I, or a pharmaceutically acceptable salt thereof, as herein defined in the manufacture of a medicament for use in the treatment of a disease or medical condition in which the damage and/or destruction of the vasculature in a warm-blooded animal (such as man) has an effect. For example, the present invention may provide a compound of the Formula I as defined in respect to the second aspect (including the preferred compound(s) of the Formula I', I", I''' and/or I''''), or a pharmaceutically acceptable thereof, in the manufacture of a medicament for use in the treatment of a disease or medical condition in which the damage and/or destruction of the vasculature in a warm-blooded animal (such as man) has an effect.

The present invention provides a method for treating a disease or medical condition in which the damage and/or destruction of the vasculature in a warm-blooded animal (such as man) has an effect which comprises administering to said animal an effective amount of a compound of the Formula I, or a pharmaceutically acceptable salt thereof, as herein defined. For example, the present invention may provide a method for treating a disease or medical condition in which the damage and/or destruction of the vasculature in a warm-blooded animal (such as man) has an effect which comprises administering to said animal an effective amount of a compound of the Formula I as defined in respect to the second aspect (including the preferred compound(s) of the Formula I', I", I''' and/or I''''), or a pharmaceutically acceptable thereof.

The present invention further provides a compound of the Formula I, or a pharmaceutically acceptable salt thereof, as herein defined for use in the treatment of a disease or medical condition in which the damage and/or destruction of the vasculature in a warm-blooded animal (such as man) has an effect. For example, the present invention may provide a compound of the Formula I as defined in respect to the second aspect (including the preferred compound(s) of the Formula I', I", I''' and/or I''''), or a pharmaceutically acceptable thereof, for use in the treatment of a disease or medical condition in which the damage and/or destruction of the vasculature in a warm-blooded animal (such as man) has an effect.

The present invention further provides the use of a compound of the Formula I, or a pharmaceutically acceptable salt thereof, as herein defined in the manufacture of a medicament for use in the treatment of a vascular proliferative disease or medical condition in a warm-blooded animal (such as man). For example, the present invention may provide a compound of the Formula I as defined in respect to the second aspect (including the preferred compound(s) of the Formula I', I", I''' and/or I''''), or a pharmaceutically acceptable thereof, in the manufacture of a medicament for use in the treatment of a vascular proliferative disease or medical condition in a warm-blooded animal (such as man).

The present invention provides a method for treating a vascular proliferative disease or medical condition in a warm-blooded animal (such as man) in need of such treatment which comprises administering to said animal an effective amount of a compound of the Formula I, or a pharmaceutically acceptable salt thereof, as herein defined. For example, the present invention may provide a method for treating a vascular proliferative disease or medical condition in a warm-blooded animal (such as man) in need of such treatment which comprises administering to said animal an effective amount of a compound of the Formula I as defined in respect to the second aspect (including the preferred compound(s) of the Formula I', I", I'" and/or I""), or a pharmaceutically acceptable thereof.

The present invention further provides a compound of the Formula I, or a pharmaceutically acceptable salt thereof, as herein defined for use in the treatment of a vascular proliferative disease or medical condition in a warm-blooded animal (such as man). For example, the present invention may provide a compound of the Formula I as defined in respect to the second aspect (including the preferred compound(s) of the Formula I', I", I'" and/or I""), or a pharmaceutically acceptable thereof, for use in the treatment of a vascular proliferative disease or medical condition in a warm-blooded animal (such as man).

Any suitable disease or medical condition in which the damage and/or destruction of the vasculature in a warm-blooded animal has an effect and/or any suitable vascular proliferative disease or medical condition may be treated according to the present invention. For example, suitable such diseases or medical conditions may be selected from one or more of a cancer, macular degeneration, proliferative retinopathy (such as proliferative diabetic retinopathy), psoriasis and/or endometriosis, particularly from a cancer, macular degeneration and/or proliferative retinopathy (such as proliferative diabetic retinopathy), more particularly from a cancer and macular degeneration.

The present invention additionally provides the use of a compound of the Formula I, or a pharmaceutically acceptable salt thereof, as herein defined in the manufacture of a medicament for use in the treatment of a cancer in a warm-blooded animal (such as man). For example, the present invention may provide a compound of the Formula I as defined in respect to the second aspect (including the preferred compound(s) of the Formula I', I", I'" and/or I""), or a pharmaceutically acceptable thereof, in the manufacture of a medicament for use in the treatment of a cancer in a warm-blooded animal (such as man).

The present invention further provides a method for treating a cancer in a warm-blooded animal (such as man) in need of such treatment, which comprises administering to said animal an effective amount of a compound of the Formula I, or a pharmaceutically acceptable salt thereof, as herein defined. For example, the present invention may provide a method for treating a cancer in a warm-blooded animal (such as man) in need of such treatment, which comprises administering to said animal an effective amount of a compound of the Formula I as defined in respect to the second aspect (including the preferred compound(s) of the Formula I', I", I'" and/or I""), or a pharmaceutically acceptable thereof.

The present invention further provides a compound of the Formula I, or a pharmaceutically acceptable salt thereof, as herein defined for use in the treatment of a cancer in a warm-blooded animal (such as man). For example, the present invention may provide a compound of the Formula I as defined in respect to the second aspect (including the preferred compound(s) of the Formula I', I", I'" and/or I""), or a pharmaceutically acceptable thereof, for use in the treatment of a cancer in a warm-blooded animal (such as man).

Cancers that may be treated according to the present invention include leukaemias, colorectal, cervical, head and neck, lung, ovarian, pancreatic, thyroid, prostate, bladder, brain, breast, liver, stomach, oesophageal and skin cancers.

The present invention additionally provides the use of a compound of the Formula I, or a pharmaceutically acceptable salt thereof, as herein defined in the manufacture of a medicament for use in the treatment of a cancer involving a solid tumour in a warm-blooded animal (such as man). For example, the present invention may provide a compound of the Formula I as defined in respect to the second aspect (including the preferred compound(s) of the Formula I', I", I'" and/or I""), or a pharmaceutically acceptable thereof, in the manufacture of a medicament for use in the treatment of a cancer involving a solid tumour in a warm-blooded animal (such as man).

The present invention further provides a method for treating a cancer involving a solid tumour in a warm-blooded animal (such as man) in need of such treatment, which comprises administering to said animal an effective amount of a compound of the Formula I, or a pharmaceutically acceptable salt thereof, as herein defined. For example, the present invention may provide a method for treating a cancer involving a solid tumour in a warm-blooded animal (such as man) in need of such treatment, which comprises administering to said animal an effective amount of a compound of the Formula I as defined in respect to the second aspect (including the preferred compound(s) of the Formula I', I", I'" and/or I""), or a pharmaceutically acceptable thereof.

The present invention further provides a compound of the Formula I, or a pharmaceutically acceptable salt thereof, as herein defined for use in the treatment of a cancer involving a solid tumour in a warm-blooded animal (such as man). For example, the present invention may provide a compound of the Formula I as defined in respect to the second aspect (including the preferred compound(s) of the Formula I', I", I'" and/or I""), or a pharmaceutically acceptable thereof, for use in the treatment of a cancer involving a solid tumour in a warm-blooded animal (such as man).

Cancers involving solid tumours that may be treated according to the present invention include colorectal, cervical, head and neck, lung, ovarian, pancreatic, thyroid, prostate, bladder, brain, breast, liver, stomach, oesophageal and skin cancers.

The present invention additionally provides the use of a compound of the Formula I, or a pharmaceutically acceptable salt thereof, as herein defined in the manufacture of a medicament for use in the treatment of macular degeneration (including age-related macular degeneration) in a warm-blooded animal (such as man). For example, the present invention may provide a compound of the Formula I as defined in respect to the second aspect (including the preferred compound(s) of the Formula I', I", I'" and/or I"", or a pharmaceutically acceptable thereof, in the manufacture of a medicament for use in the treatment of macular degeneration (including age-related macular degeneration) in a warm-blooded animal (such as man).

The present invention further provides a method for treating macular degeneration (such as age-related macular degeneration) in a warm-blooded animal (such as man) in need of such treatment, which comprises administering to said animal an effective amount of a compound of the Formula I, or a pharmaceutically acceptable salt thereof, as herein defined. For example, the present invention may provide a method for treating macular degeneration (such as age-related macular degeneration) in a warm-blooded animal (such as man) in need of such treatment, which comprises administering to said animal an effective amount of a compound of the Formula I as defined in respect to the second aspect (including the preferred compound(s) of the Formula I', I", I'" and/or I""), or a pharmaceutically acceptable thereof.

The present invention further provides a compound of the Formula I, or a pharmaceutically acceptable salt thereof, as herein defined for use in the treatment of macular degeneration (such as age-related macular degeneration) in a warm-blooded animal (such as man). For example, the present invention may provide a compound of the Formula I as defined in respect to the second aspect (including the preferred compound(s) of the Formula I', I", I''' and/or I''''), or a pharmaceutically acceptable thereof, for use in the treatment of macular degeneration (such as age-related macular degeneration) in a warm-blooded animal (such as man).

The present invention further provides a pharmaceutical composition which comprises a compound of the Formula I, or a pharmaceutically acceptable thereof, as defined herein in association with a pharmaceutically acceptable excipient, diluent or carrier. For example, the present invention may provide a pharmaceutical composition which comprises a compound of the Formula I as defined in respect to the second aspect (including the preferred compound(s) of the Formula I', I", I''' and/or I''''), or a pharmaceutically acceptable thereof, in association with a pharmaceutically acceptable excipient, diluent or carrier. Suitable pharmaceutically acceptable excipients, diluents and carriers include gelatine, water, petroleum, animal or vegetable oils, mineral or synthetic oil, saline, glycols such as ethylene glycol, propylene glycol and polyethylene glycol, or encapsulation by liposomes.

As the skilled person would appreciate, the compositions of the present invention may be in any suitable form. For example, the compositions may be in a form suitable for oral administration (for example as tablets, lozenges, capsules, aqueous or oily suspensions, emulsions, dispersible powders or granules, syrups or elixirs), for topical administration (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the present invention may be obtained by conventional procedures using conventional pharmaceutical excipients, diluents and/or carriers which would be well known to a person skilled in the art. Thus, the present invention further provides a process for the preparation of a pharmaceutical composition, which process comprises mixing a compound of the Formula I, or a pharmaceutically acceptable salt thereof, with a pharmaceutically acceptable excipient, diluent or carrier. For example, the present invention may provide a process for the preparation of a pharmaceutical composition, which process comprises mixing a compound of the Formula I as defined in respect to the second aspect (including the preferred compound(s) of the Formula I', I", I''' and/or I''''), or a pharmaceutically acceptable salt thereof, with a pharmaceutically acceptable excipient, diluent or carrier.

The amount of active ingredient that is combined with the pharmaceutical excipient, diluent or carrier to produce a single dosage form will vary depending upon the host treated and the particular route of administration, as well as depending on the particular disease or condition being treated.

As the skilled person would appreciate, the compounds of the Formula I, or a pharmaceutically acceptable thereof, as herein defined may be administered in the form of a pro-drug, by which we mean a compound that is broken down in a warm-blooded animal (such as man) to release a compound of the Formula I. A pro-drug may, for example, be used to alter the physical properties and/or the pharmacokinetic properties of a compound of the Formula I, or a pharmaceutically acceptable thereof. A pro-drug can be formed when the compound of the Formula I, or a pharmaceutically acceptable thereof, contains a suitable group or substituent to which a property-modifying group can be attached. A suitable pharmaceutically acceptable pro-drug of a compound of the Formula I, or a pharmaceutically acceptable thereof, as herein defined should be suitable for administration to the body of a warm-blooded animal (such as man) without undesirable pharmacological activities and without undue toxicity.

Accordingly, the present invention includes those compounds of the Formula I, or a pharmaceutically acceptable thereof, as herein defined that are produced by organic synthetic means and that are produced in the body of a warm-blooded animal (such as man) by way of metabolism of a precursor compound, for example by way of cleavage of a pro-drug thereof.

The compounds of the Formula I, or a pharmaceutically acceptable thereof, as herein defined may be applied as a sole therapy or may involve a combination therapy which includes for example a conventional surgery, radiotherapy and/or chemotherapy in addition to treatment with a compound of the Formula I, or a pharmaceutically acceptable thereof. Chemotherapy compounds that may be administered in combination with the compounds of the present invention include one or more of carboplatin, paclitaxel and avastin, although any suitable chemotherapy compound(s) may be used. Such combination treatment may be achieved by way of the simultaneous, sequential or separate dosing of the individual components of the treatment.

The present invention further provides a pharmaceutical product comprising a compound of the Formula I, or a pharmaceutically acceptable thereof, as herein defined and an additional agent for the conjoint treatment of a cancer, especially for the treatment of a cancer involving a solid tumour in a warm-blooded animal (such as man). For example, the present invention may provide a pharmaceutical product comprising a compound of the Formula I as defined in respect to the second aspect (including the preferred compound(s) of the Formula I', I", I''' and/or I''''), or a pharmaceutically acceptable thereof, and an additional agent for the conjoint treatment of a cancer, especially for the treatment of a cancer involving a solid tumour in a warm-blooded animal (such as man).

Although the compounds of the Formula I, or a pharmaceutically acceptable thereof, are primarily of value as therapeutic agents for use in warm-blooded animals (such as man) they are also useful whenever it is required to produce a vascular damaging effect. They may be useful as pharmacological standards for use in the development of new biological tests and in the search for new pharmacological agents.

References herein to a compound of the Formula I are intended include all definitions of such a compound, for example as defined herein in relation to the first and second aspects of the present invention as well as in relation to specific compounds, for example of the Formula I', I", I''', I'''', IA and/or IB, unless otherwise indicated. Specific references herein the compounds of the Formula I as defined in relation to the first or second aspect of the present invention and/or in relation to preferred compounds of the Formula I', I", I''', I'''', IA and/or IB are intended to relate to those particular compounds only.

The invention will now be illustrated by the following non-limiting Examples in which, unless stated otherwise:
(i) temperatures are given in degrees Celsius (° C.);
(ii) operations were carried out at room or ambient temperature, by which we mean a temperature in the range of from 18 to 25° C.;
(iii) in general, the course of reactions was followed by analytical thin-layer chromatography (TLC) was carried out using Merck silica gel 60 on aluminium plates and the chromatograms were visualised using UV light (254 nm), acidified aqueous potassium permanganate or vanillin dip;
(iv) preparative TLC was carried out on Merck silica gel 60 on aluminium plates with concentrating zone;
(v) column chromatography was carried out using the flash technique on BDH silica gel 60 (4360 µm);
(vi) solvent ratios are given in volume:volume (v/v) terms;
(vii) reaction times are given for illustration only;
(viii) final products had satisfactory proton nuclear magnetic resonance (NMR) spectra and/or mass spectral data;
(ix) yields are given for illustration only and are not necessarily those which can be obtained by diligent process development (preparations being repeated if more material was required);
(x) chemical symbols have their usual meanings; SI units and symbols are used;
(xi) unless stated otherwise compounds containing an asymmetrically substituted carbon atom have not been resolved;
(xii) all air and moisture sensitive reactions were carried out using standard inert atmosphere techniques under argon, dried with an anhydrous $CaCl_2$ drying tube and freed from traces of oxygen using an Oxysept cartridge (both Aldrich);
(xiii) all glassware was pre-dried in an oven (at a temperature of around 130° C.) and cooled under vacuum;
(xiv) commercial starting materials and solvents were used as supplied without purification. Anhydrous solvents were either purchased from Aldrich and kept in Sureseal bottles over 3 Å molecular sieves or were dried using conventional methods (for example as described in Perrin, D. D.; Armarego, W. L. F.; Perrin, D. R. *Purification of Laboratory Chemicals, 2nd.* Edition, Pergamon, Oxford, 1980); tetrahydrofuran and N,N,N',N'-tetramethylethylenediamine were dried using sodium-benzophenone ketyl under argon;
(xv) melting points (m.p.) were determined using a Buchi 512 or Electrothermal 9100 apparatus and are uncorrected;
(xvi) IR spectra were of neat films on NaCl plates and were recorded on either a Perkin Elmer 171 OFT or a Nicolet Nexus 670/870 FT-IR spectrometer;
(xvii) NMR spectra were recorded on Bruker DPX200 ($^1$H at 200 MHz), DPX300 ($^1$H at 300 MHz, $^{13}$C at 75 MHz) or DPX400 ($^1$H at 400 MHz, $^{13}$C at 100 MHz) instruments using deuterium resonance as the internal lock reference; delta values are given in parts per million (ppm) and J values are quoted to the nearest 0.1 Hz; Assignments for $^1$H NMR spectra were aided by HMQC NMR where noted and assignments for $^{13}$C were aided by the use of DEPT-135 spectra; the following abbreviations have been used: s, singlet; d, doublet; t, triplet; q, quartet; m, multiplet; br, broad;
(xviii) mass spectra were measured on a Micromass LCT instrument using electrospray (ES) ionisation and a Waters 2790 separation module with TOF fragment detection and High-resolution mass spectra were recorded on a ThermoFinnigan MAT95XP instrument; where chemical ionisation (CI) mass spectra are indicated, a Micromass Trio 2000 instrument was used; when the mass ion quoted is (MH)$^+$ this refers to the protonated mass ion, is M$^+$ this refers to the mass ion generated by loss of an electron and is M–H$^+$ this refers to the mass ion generated by loss of a proton;
(xix) Evaporations, as referred to in the following experiments, were carried out under reduced pressure with a Büchi rotary evaporator with a water or dry ice condenser as necessary;
(xx) the following abbreviations have been used:
  THF tetrahydrofuran;
  DMF N,N-dimethylformamide;
  Ether diethyl ether; and
  TMEDA N,N,N',N'-tetramethylethylenediamine

EXAMPLE 1

1,2,3,9-Tetramethoxy-5,7-dihydrodibenzo[c,e]ox-epine

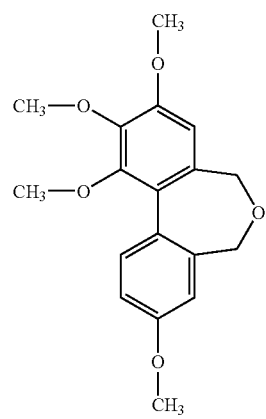

A solution of (4,4',5,6-tetramethoxybiphenyl-2,2'-diyl) dimethanol (170 mg, 0.51 mmol) in THF (2 mL), 2M HCl (2 mL) and concentrated hydrochloric acid (1 mL) was stirred under reflux for 3 hours. Water (15 mL) and ethyl acetate (15 mL) were added to the reaction mixture, the layers were separated and the aqueous layer was extracted with ethyl acetate (2×10 mL). The extracts were combined, dried over $Na_2SO_4$, filtered and concentrated in vacuo. Flash chromatography of the residue over silica gel (20 g), eluting with hexane-ethyl acetate (4:1), yielded the title compound as a white solid (150 mg, 93%); m.p. 151-153° C.; Elemental Analysis Found: C, 68.5; H, 6.5 ($C_{18}H_{20}O_5$ requires C, 68.34; H, 6.37%); NMR Spectrum $\delta_H$ (300 MHz, $CDCl_3$) 7.63 (1H, d, J 8.4 Hz, 11-H), 6.98 (1H, dd, J 2.6, 8.4 Hz, 10-H), 6.96 (1H, d, J 2.6 Hz, 8-H), 6.75 (1H, s, 4-H), 4.42 (2H, m), 4.08 (2H, m), 3.94 (3H, s, $OCH_3$), 3.91 (3H, s, $OCH_3$), 3.86 (3H, s, $OCH_3$), 3.65 (3H, s, $OCH_3$); NMR Spectrum $\delta_C$ (75 MHz, $CDCl_3$) 55.7, 56.4, 61.2, 61.5, 68.1, 109.1, 114.2, 114.8, 126.7, 129.7, 131.1, 131.4, 136.8, 143.1, 150.9, 153.1, 159.4; $v_{max}$/cm$^{-1}$ (thin film) 2963, 2936, 2858, 2839, 1612, 1491, 1456, 1332, 1243, 1150, 1104, 1052, 1006; m/z (ES) 380 ($MNa_2H_2O^+$, 100%), 287 (MH$^+$—$CH_2O$, 100); R$_f$ (hexane-ethyl acetate 3:1) 0.39.

The (4,4',5,6-tetramethoxybiphenyl-2,2'-diyl)dimethanol starting material was made as follows:

To a stirred refluxing solution of 3,4,5-trimethoxybenzaldehyde (17.0 g, 86.6 mmol) in water (3 mL) and chloroform (100 mL) was added a solution of bromine (14.7 g, 92 mmol) in chloroform (30 mL) dropwise. The solution was heated under reflux overnight, cooled, washed with water (2×100 mL) and saturated aqueous sodium hydrogen carbonate (50 mL), dried over $MgSO_4$, filtered and evaporated. The residual orange oil (27 g) crystallised on standing. The solid was washed with petroleum ether, b.p. 40-60° C., to obtain 2-bromo-3,4,5-trimethoxybenzaldehyde as white crystals (23.4 g, 98%); m.p. 69° C. (literature value 69.5-71° C., see Brown, E.; Robin, J.-P.; Dhal, R. Tetrahedron 1982, 38, 2569-2579); NMR Spectrum $\delta_H$ (300 MHz, $CDCl_3$) 10.40 (1H, s, 1-CHO), 7.29 (1H, s, 6-H), 4.00 (3H, s, $OCH_3$), 3.95 (3H, s, $OCH_3$) and 3.93 (3H, s, $OCH_3$); NMR Spectrum $\delta_C$ (75 MHz, $CDCl_3$) 56.6, 61.6, 106.9, 126.1, 128.1, 149.2, 150.3, 152.8, 189.2; $v_{max}$/cm$^{-1}$ (thin film) 2940, 2843, 1685 (C=O), 1588, 1480, 1460, 1386, 1317, 1196, 1161, 1134, 1103 and 1002 (data in accordance with published values, see Brown, E.; Robin, J.-P.; Dhal, R. Tetrahedron 1982, 38, 2569-2579); $R_f$(hexane-ethyl acetate 4:1) 0.50.

To a stirred solution of 2-bromo-5-methoxybenzoic acid (Aldrich 384003; 5.0 g, 21.6 mmol) in methanol (80 mL) was added concentrated hydrochloric acid (2 mL) and the mixture was heated under reflux for 18 hours. The resulting solution was cooled, the solvent was removed in vacuo, water (100 mL) was added and the mixture was extracted with ethyl acetate (2×100 mL). The combined extracts were washed with saturated aqueous sodium hydrogen carbonate, dried over MgSO$_4$, filtered and evaporated to obtain methyl 2-bromo-5-methoxybenzoate as a light brown oil (4.50 g, 85%); NMR Spectrum $\delta_H$ (300 MHz, CDCl$_3$) 7.53 (1H, d, J 8.8 Hz, 3-H), 7.32 (1H, d, J 3.0 Hz, 6-H), 6.89 (1H, dd, J 3.0, 8.8 Hz, 4-H), 3.94 (3H, s, Ar OCH$_3$) and 3.82 (3H, s, CO$_2$CH$_3$) (data in accordance with published values, see Barhate, N. B.; Gajare, A. S.; Wakharkar, R. D.; Bedekar, A. V. Tetrahedron 1999, 55, 11127-11142); $v_{max}$/cm$^{-1}$ (thin film) 2951, 1732 (C=O), 1592, 1472, 1433, 1289, 1250, 1227, 1099, 1017, 975, 823, 792 (data in accordance with published values, see Barhate, N. B.; Gajare, A. S.; Wakharkar, R. D.; Bedekar, A. V. Tetrahedron 1999, 55, 11127-11142); $R_f$(hexane-ethyl acetate 5:1) 0.58.

To a suspension of copper bronze (7.88 g, 122 mmol) in anhydrous DMF (12 mL) was added a solution of 2-bromo-3,4,5-trimethoxybenzaldehyde (3.36 g, 12.2 mmol) and methyl 2-bromo-5-methoxybenzoate (3.00 g, 12.2 mmol) in anhydrous DMF (6 mL) and the suspension was stirred at 165° C. for 3 hours. The reaction was cooled, diluted with ethyl acetate (250 mL) and the resulting suspension was filtered through Celite® (40 g). The solvent was removed in vacuo, leaving a brown oil (5.0 g) of which a portion (2.0 g) was purified by chromatographed over silica gel (200 g), eluting with hexane-ethyl acetate (gradient 8:1 to 6:1), followed by crystallisation from petroleum ether, which yielded methyl 6'-formyl-2',3',4,4'-tetramethoxybiphenyl-2-carboxylate (1.10 g, 63%); m.p. 62-64° C.; Elemental Analysis Found: C, 63.5; H, 5.7 (C$_{19}$H$_{20}$O$_7$ requires C, 63.33; H, 5.59%); NMR Spectrum $\delta_H$ (300 MHz, CDCl$_3$) 9.60 (1H, s, CHO), 7.60 (1H, d, J 2.6 Hz, 3-H), 7.35 (1H, s, 5'-H), 7.18 (1H, d, J 8.4 Hz, 6-H), 7.18 (1H, dd, J 2.6, 8.4 Hz, 5-H), 3.97 (3H, s, Ar OCH$_3$), 3.95 (3H, s, Ar OCH$_3$), 3.91 (3H, s, Ar OCH$_3$) and 3.55 (3H, s, CO$_2$CH$_3$); NMR Spectrum $\delta_C$ (75 MHz, CDCl$_3$) 52.5, 56.0, 56.4, 61.1, 61.4, 105.2, 115.5, 118.0, 126.6, 129.8, 132.8, 134.2, 134.3, 147.6, 151.2, 153.3, 159.6, 167.4, 191.2; $v_{max}$/cm$^{-1}$ (thin film) 2944, 2835, 1724 (C=O), 1685 (C=O), 1592, 1480, 1394, 1332, 1289, 1223, 1192, 1145, 1099, 1072, 1002, 928, 850, 757; m/z (ES) 424 (MNa$_2$H$_2$O$^+$, 100%), 383 (MNa$^+$, 80); $R_f$(hexane-ethyl acetate 5:1) 0.19. Also isolated was the symmetrical biaryl dimethyl 4,4'-dimethoxy-2,2'-diphenoate (0.25 g); m.p. 76-77° C. (literature value 78° C., see Bunton, C. A.; Kenner, G. W.; Robinson, M. J. T.; Webster, B. R. Tetrahedron 1963, 19, 1001-1010); NMR Spectrum $\delta_H$ (300 MHz, CDCl$_3$) 7.48 (2H, d, J=2.6 Hz, 3 and 3'-H), 7.10 (2H, d, J=8.4 Hz, 6,6'-H), 7.04 (2H, dd, J 2.6, 8.4 Hz, 5,5'-H), 3.90 (6H, s, 4,4'-OCH$_3$) and 3.64 (6H, s, 2,2'-CO$_2$CH$_3$) (data in accordance with published values, see Bunton, C. A.; Kenner, G. W.; Robinson, M. J. T.; Webster, B. R. Tetrahedron 1963, 19, 1001-1010); $R_f$ (hexane-ethyl acetate 5:1) 0.27.

To a solution of crude methyl 6'-formyl-2',3',4,4'-tetramethoxybiphenyl-2-carboxylate (55% pure by $^1$H NMR spectroscopy; 3.0 g, 4.6 mmol) in methanol (100 mL) was added sodium borohydride (0.61 g, 16.0 mmol) and the solution was stirred at room temperature for 1 hour. Water (120 mL) and ethyl acetate (120 mL) were then added to the reaction, the layers were separated and the aqueous layer was extracted with ethyl acetate (2×80 mL). The combined extracts were dried over Na$_2$SO$_4$ and filtered. The solvent was removed in vacuo and the residue was purified by flash chromatography over silica gel (150 g), eluting with hexane-ethyl acetate (1:1), which yielded a clear oil (1.30 g). This was shown by $^1$H NMR spectroscopy to be a 3:1 mixture of methyl 6'-(hydroxymethyl)-2',3',4,4'-tetramethoxybiphenyl-2-carboxylate and 3,4,5-trimethoxybenzyl alcohol (identified by TLC and $^1$H NMR comparison with an authentic sample). This crude methyl 6'-(hydroxymethyl)-2',3',4,4'-tetramethoxybiphenyl-2-carboxylate (1.10 g, 66%), which was used without further purification in the next reaction, had NMR Spectrum $\delta_H$(300 MHz, CDCl$_3$) 7.46 (1H, d, J 2.1 Hz, 3-H), 7.16-7.07 (2H, m, 5,6-H), 6.87 (1H, s, 5'-H), 4.34 (1H, d, J 11.7 Hz, 6'-CH$_A$OH), 4.25 (1H, dd, J 5.2, 11.7 Hz, 6'-CH$_B$OH), 3.92 (3H, s, Ar OCH$_3$) 3.89 (3H, s, Ar OCH$_3$), 3.88 (3H, s, Ar OCH$_3$), 3.71 (3H, s, Ar OCH$_3$), 3.56 (3H, s, 2-CO$_2$CH$_3$), 2.44 (1H, br s, 6'-CH$_2$OH); $R_f$ (hexane-ethyl acetate 1:1) 0.30.

To a solution of lithium borohydride (78 mg, 3.6 mmol) in dry ether (10 mL) under argon was added a solution of methyl 6'-(hydroxymethyl)-2',3',4,4'-tetramethoxybiphenyl-2-carboxylate (1.3 g, 85% pure, 2.9 mmol) in dry ether (10 mL) and the mixture was then heated under reflux for 18 hours. After being cooled to room temperature, the mixture was acidified with concentrated hydrochloric acid (1 mL), diluted with water (50 mL) and extracted with ether (3×30 mL). The combined extracts were dried over MgSO$_4$, filtered and evaporated to give a crude solid (1.2 g) which was purified by flash chromatography over silica gel (60 g), eluting with hexane-ethyl acetate (2:1), followed by recrystallisation (twice) from ethyl acetate-hexane. This gave (4,4',5,6-tetramethoxybiphenyl-2,2'-diyl)dimethanol (600 mg, 62%); m.p. 137-139° C.; Elemental Analysis Found: C, 64.9; H, 6.7 (C$_{18}$H$_{22}$O$_6$ requires C, 64.66; H, 6.63%); NMR Spectrum $\delta_H$ (300 MHz, CDCl$_3$) 7.05 (2H, m, 3,6-H), 6.90 (1H, dd, J 2.5, 9.5 Hz, 5-H), 6.87 (1H, s, 5'-H), 4.30 (2H, s, CH$_2$OH), 4.28 (2H, s, CH$_2$OH), 3.93 (3H, s, OCH$_3$), 3.91 (3H, s, OCH$_3$) 3.88 (3H, s, OCH$_3$), 3.55 (6H, s, 2×OCH$_3$), 3.05 (1H, br s, CH$_2$OH), 2.59 (1H, br s, CH$_2$OH); NMR Spectrum $\delta_C$ (75 MHz, CDCl$_3$) 55.7, 56.4, 61.4 (two signals), 63.3, 64.2, 108.6, 114.0, 115.1, 126.6, 127.6, 131.8, 135.5, 141.3, 142.0, 151.5, 153.4, 159.7; $v_{max}$/cm$^{-1}$ (nujol mull) 3266, 2924, 2846, 1612, 1596, 1484, 1460, 1402, 1386, 1332, 1289, 1250, 1200, 1157, 1095, 1049, 998; m/z (ES) 398 (MNa$_2$H$_2$O$^+$), 357 (75%, MNa$^+$); $R_f$(hexane-ethyl acetate 1:2) 0.28.

EXAMPLE 2

5,7-Dihydro-1,2,3-trimethoxybenzo[d][1,3]dioxolo[4,5-h][2]benzoxepin

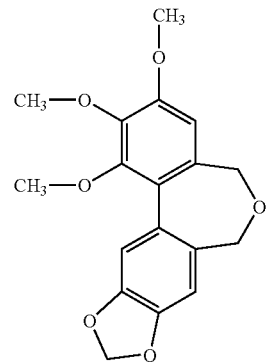

A solution of (6-(6-(hydroxymethyl)-2,3,4-trimethoxyphenyl)benzo[d][1,3]dioxol-5-yl)methanol (170 mg, 0.48 mmol) in THF (2 mL), 2M HCl (2 mL) and concentrated hydrochloric acid (1 mL) was stirred under reflux for 3 hours. Water (15 mL) and ethyl acetate (15 mL) were added to the reaction, the layers were separated and the aqueous layer was extracted with ethyl acetate (2×10 mL). The extracts were combined, dried over $Na_2SO_4$, filtered and concentrated in vacuo. Flash chromatography of the residue over silica gel (20 g), eluting with hexane-ethyl acetate (4:1), followed by crystallisation (ethyl acetate) yielded the title compound as large clear crystals (103 mg, 64%); m.p. 154-156° C.; Elemental Analysis Found: C, 65.3; H, 5.5 ($C_{18}H_{18}O_6$ requires C, 65.45; H, 5.49%); NMR Spectrum $\delta_H$ (300 MHz, $CDCl_3$) 7.21 (1H, s, 12-H), 6.98 (1H, s, 8-H), 6.96 (1H, s, 4-H), 6.75 (1H, s, 4-H), 6.04 (2H, d, J 4.8 Hz, 10-$H_2$), 4.40 (2H, d, J 11.2 Hz, 5-$H_2$), 4.04 (1H, d, J 10.8 Hz, 7-$H_A$), 4.01 (1H, d, J 10.8 Hz, 7-$H_B$), 3.96 (3H, s, $OCH_3$), 3.91 (3H, s, $OCH_3$), 3.71 (3H, s, $OCH_3$); NMR Spectrum $\delta_C$ (75 MHz, $CDCl_3$) 56.3, 61.2, 61.5, 67.6, 67.8, 101.6, 109.0, 109.9, 110.2, 126.8, 129.5, 131.3, 131.7, 143.0, 147.3, 147.7, 150.8, 153.3; $\nu_{max}/cm^{-1}$ (thin film) 2967, 2932, 2866, 1600, 1484, 1460, 1414, 1324, 1239, 1146, 1107, 1045; m/z (ES) 301 ($MH^+$—$CH_2O$, 100%); $R_f$(hexane-ethyl acetate 4:1) 0.28.

The (6-(6-(hydroxymethyl)-2,3,4-trimethoxyphenyl)benzo[d][1,3]dioxol-5-yl)methanol starting material was made as follows:

To a suspension of copper bronze (2.81 g, 43.6 mmol) in anhydrous DMF (5 mL) was added a solution of 2-bromo-3,4,5-trimethoxybenzaldehyde (1.2 g, 4.36 mmol) and 2-bromo-4,5-methylenedioxybenzaldehyde (1.00 g, 4.36 mmol) in anhydrous DMF (3 mL) and the suspension was stirred at 165° C. for 3 hours. The reaction was cooled, diluted with ethyl acetate (100 mL) and the resulting suspension was filtered through Celite® (15 g). The solvent was removed in vacuo and the residue was chromatographed over silica gel (50 g), eluting with hexane-ethyl acetate (6:1), which yielded crude 6-(6-formyl-2,3,4-trimethoxyphenyl)benzo[d][1,3]dioxole-5-carbaldehyde as a mixture (10:1 by $^1$H NMR spectroscopy) with 4,4',5,5',6,6'-hexamethoxybiphenyl-2,2'-dicarbaldehyde. Recrystallisation twice from ethyl acetate yielded pure 6-(6-formyl-2,3,4-trimethoxyphenyl)benzo[d][1,3]dioxole-5-carbaldehyde (330 mg, 22%); m.p. 142-143° C. (literature value 138-142° C. (benzene), see Brown, E.; Robin, J.-P.; Dhal, R. Tetrahedron 1982, 38, 2569-2579); Elemental Analysis Found: C, 63.0; H, 4.8 ($C_{18}H_{16}O_7$ requires C, 62.79; H, 4.68%); NMR Spectrum $\delta_H$ (300 MHz, $CDCl_3$) 9.64 (1H, s, CHO), 9.60 (1H, s, CHO), 7.51 (1H, s, 4-H), 7.40 (1H, s, 7-H), 6.74 (1H, s, 5'-H), 6.16 (2H, s, 2-H), 4.00 (3H, s, $OCH_3$), 3.98 (3H, s, $OCH_3$), 3.65 (3H, s, $OCH_3$); NMR Spectrum $\delta_C$ (100 MHz, $CDCl_3$) 56.6, 61.4, 61.5, 102.8, 106.2, 107.0, 112.2, 129.5, 130.7, 130.8, 133.8, 147.7, 148.9, 151.6, 152.5, 154.3, 189.8, 190.2; $\nu_{max}/cm^{-1}$ (thin film) 2940, 2850, 1685 (C=O), 1612, 1588, 1476, 1386, 1332, 1250, 1137; m/z (ES) 389 ($MNa_2H_2O^+$, 100%), 367 ($MNa^+$, 40); $R_f$(hexane-ethyl acetate 5:1) 0.21.

To a solution of crude 6-(6-formyl-2,3,4-trimethoxyphenyl)benzo[d][1,3]dioxole-5-carbaldehyde (265 mg, 0.77 mmol) in methanol (7 mL) was added sodium borohydride (80 mg, 2.1 mmol) and the solution was stirred at room temperature for 1 hour. Water (30 mL) and ethyl acetate (30 mL) were then added to the reaction, the layers were separated and the aqueous layer was extracted with ethyl acetate (2×30 mL). The combined extracts were dried over $Na_2SO_4$ and filtered. The solvent was removed in vacuo and the residue was purified by flash chromatography over silica gel (40 g), eluting with hexane-ethyl acetate (1:2), followed by crystallisation (ethyl acetate), which yielded (6-(6-(hydroxymethyl)-2,3,4-trimethoxyphenyl)benzo[d][1,3]dioxol-5-yl)methanol as a white solid (230 mg, 86%); m.p. 123-124° C.; High Resolution Mass Spectrometry Found: $M+Na^+$ 371.1105 ($C_{18}H_{20}O_7Na$ requires 371.1107); NMR Spectrum $\delta_H$ (300 MHz, $CDCl_3$) 7.00 (2H, s, 7-H), 6.88 (1H, s, 4-H), 6.63 (1H, s, 5'-H), 6.04 (2H, s, 2-H), 4.30 (2H, m, $CH_2OH$), 4.21 (2H, m, $CH_2OH$), 3.93 (3H, s, $OCH_3$), 3.91 (3H, s, $OCH_3$), 3.62 (3H, s, $OCH_3$); NMR Spectrum $\delta_C$ (75 MHz, $CDCl_3$) 56.4, 61.4, 61.5 ($CH_2$), 63.1 ($CH_2$), 63.7, 101.7, 108.7, 110.4, 110.6, 126.6, 129.1, 133.8, 135.5, 142.0, 147.5, 147.8, 151.4, 153.5; $\nu_{max}/cm^{-1}$ (thin film) 3254, 2944, 2889, 1603, 1480, 1410, 1328, 1235, 1146, 1111, 1033, 928; m/z (ES) 412 ($MNa_2H_2O^+$, 100%), 371 ($MNa^+$, 60); $R_f$(hexane-ethyl acetate 1:2) 0.14.

EXAMPLE 3

3,9,10,11-Tetramethoxy-5,7-dihydrodibenzo[c,e]oxepin-4-ol

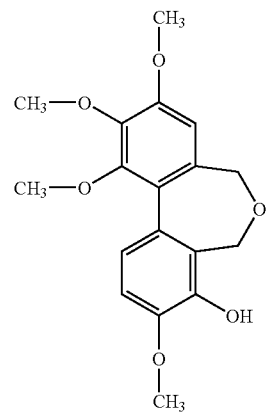

A solution of 2,6'-bis(hydroxymethyl)-4,2',3',4'-tetramethoxybiphenyl-3-yl methanesulfonate (155 mg, 0.362 mmol) in THF (2 mL), 2M HCl (2 mL) and concentrated hydrochloric acid (1 mL) was stirred under reflux for 3 hours. Water (15 mL) and ethyl acetate (15 mL) were added to the reaction, the layers were separated and the aqueous layer was extracted with ethyl acetate (2×10 mL). The extracts were combined, dried over $Na_2SO_4$, filtered and concentrated in vacuo. Flash chromatography of the residue over silica gel (20 g), eluting with hexane-ethyl acetate (gradient 3:1 to 1:1), yielded 3,9,10,11-tetramethoxy-5,7-dihydrobenzo[c,e]oxepin-4-yl methanesulfonate as a white solid (110 mg, 74%); m.p. 154-156° C.; Elemental Analysis Found: C, 55.7; H, 5.2 ($C_{19}H_{22}O_8S$ requires C, 55.60; H, 5.40%); NMR Spectrum $\delta_H$ (300 MHz, $CDCl_3$) 7.63 (1H, d, J 8.7 Hz, 1-H), 6.98 (1H, d, J 8.7 Hz, 2-H), 6.77 (1H, s, 8-H), 5.03 (1H, d, J 11.6 Hz, 5-H), 4.44 (1H, d, J 11.3 Hz, 7-H), 4.07-3.88 (2H, br m, 5-H, 7-H), 3.99 (3H, s, $OCH_3$), 3.96 (3H, s, $OCH_3$), 3.94 (3H, s, $OCH_3$), 3.70 (3H, s, $OCH_3$), 3.42 (3H, s, $SCH_3$); NMR Spectrum $\delta_C$ (75 MHz, $CDCl_3$) 59.8, 56.5, 56.6, 60.6, 61.3, 61.5, 68.2, 109.2, 112.6, 125.7, 129.3, 130.5, 131.1, 131.3, 137.5, 143.1, 150.9, 151.5, 153.6; $\nu_{max}/cm^{-1}$ (thin film) 2940, 1604, 1573, 1484, 1460, 1367, 1282, 1161, 1118, 1072, 1060, 909, 831; m/z (ES) 474 ($MNa_2H_2O^+$, 100%), 433 ($MNa^+$, 19), 411 ($MH^+$, 4); $R_f$(hexane-ethyl acetate 2:1) 0.32.

To a solution of 3,9,10,11-tetramethoxy-5,7-dihydrobenzo[c,e]oxepin-4-yl methanesulfonate (85 mg, 0.231 mmol) in dioxane (0.25 mL) and methanol (0.25 mL) was added aqueous 3M potassium hydroxide (0.5 mL) and the mixture was stirred overnight at 50° C. The solution was diluted with 2M aqueous hydrochloric acid (2 mL) at 0° C., extracted with dichloromethane (3×5 mL), washed with saturated aqueous sodium hydrogen carbonate (5 mL), dried over $MgSO_4$, filtered and evaporated. The residual white solid was chromatographed over silica gel (30 g), eluting with hexane-ethyl acetate (2:1), to obtain the title compound (62 mg, 90%); m.p. 145-147° C.; Elemental Analysis Found: C, 64.8; H, 6.1 ($C_{18}H_{20}O_6$ requires C, 65.05; H, 6.07%); NMR Spectrum $\delta_H$ (300 MHz, $CDCl_3$) 7.20 (1H, d, J 8.4 Hz, 1-H), 6.93 (1H, d, J 8.4 Hz, 2-H), 6.75 (1H, s, 4-H), 5.84 (1H, s, 4-OH), 5.14 (1H, d, J 11.4 Hz, 5-$CH_A$), 4.39 (1H, d, J 11.4 Hz, 5-$CH_B$), 4.04 (1H, d, J 11.3 Hz, 7-$CH_C$), 3.95 (3H, s, $OCH_3$), 3.93 (3H, s, $OCH_3$), 3.90 (3H, s, $OCH_3$), 3.84 (1H, d, J 11.3 Hz, 7-$CH_D$), 3.65 (3H, s, $OCH_3$); NMR Spectrum $\delta_C$ (75 MHz, $CDCl_3$) 56.4, 56.5, 59.6, 61.2, 61.5, 68.2, 109.2, 110.3, 121.2, 121.5, 126.8, 131.1, 131.6, 143.1, 143.8, 145.9, 151.1, 153.1; $\delta_C$ DEPT (75 MHz, $CDCl_3$) 56.42, 56.50, 59.63 ($CH_2$), 61.21, 61.50, 68.21 ($CH_2$), 109.14, 110.33, 121.21; $\nu_{max}$/cm$^{-1}$ 3394, 2932, 2858, 1600, 1480, 1344, 1270, 1250, 1150, 1115, 1087, 1056; m/z (ES) 396 ($MNa_2H_2O^+$, 55%), 355 ($MNa^+$, 4), 315 ($MH^+-H_2O$, 100), 303 ($MH^+-CH_2O$, 17); $R_f$(hexane-ethyl acetate 1:1) 0.42. The 2,6'-bis(hydroxymethyl)-4,2',3',4'-tetramethoxybiphenyl-3-yl methanesulfonate starting material was prepared as follows:

To a stirred solution of 6-bromo-2-hydroxy-3-methoxybenzaldehyde (0.33 g, 1.43 mmol) and triethylamine (0.17 g, 1.71 mmol) in dichloromethane (5 mL) was added methanesulfonyl chloride (0.19 g, 2.3 mmol) at 0° C., the reaction was stirred at 0° C. for 10 minutes and then at room temperature for 30 minutes, by which time a brown colour had developed. Water (20 mL) was added, the mixture was extracted with ethyl acetate (2×20 mL). The combined extract was washed with brine, dried over $MgSO_4$, filtered and evaporated to give a crude solid (0.42 g). Flash chromatography over silica gel (60 g), eluting with hexane-ethyl acetate (3:1), gave 3-bromo-2-formyl-6-methoxyphenyl methanesulfonate (320 mg, 72%) and 5-bromo-8-methoxybenzo[e][1,2]oxathiine 2,2-dioxide (90 mg, 22%) as white solids. The 3-bromo-2-formyl-6-methoxyphenyl methanesulfonate had m.p. 95-97° C.; NMR Spectrum $\delta_H$ (300 MHz, $CDCl_3$) 10.30 (1H, s, CHO), 7.58 (1H, d, J 8.9 Hz, 4-H), 7.11 (1H, d, J 8.9 Hz, 5-H), 3.95 (3H, s, $OCH_3$), 3.57 (3H, s, $SCH_3$); NMR Spectrum $\delta_C$ (75 MHz, $CDCl_3$) 40.4, 57.1, 115.5, 118.3, 129.2, 133.2, 138.9, 152.9, 190.0; $\nu_{max}$/cm$^{-1}$ (thin film) 1705, 1565, 1468, 1399, 1363, 1293, 1219, 1165, 1130, 971, 878, 800; m/z (ES) 374/372 ($MNa_2H_2O^+$, 100%), 333/331 ($MNa^+$, 80); $R_f$(hexane-ethyl acetate 1:1) 0.35. The 5-bromo-8-methoxybenzo[e][1,2]oxathiine 2,2-dioxide had m.p. 186-188° C.; Elemental Analysis Found: C, 37.3; H, 2.2; S, 10.9; Br, 27.2 ($C_9H_7BrO_4S$ requires C, 37.13; H, 2.42; S, 11.01; Br, 27.45%); NMR Spectrum $\delta_H$ (300 MHz, $CDCl_3$) 7.62 (1H, d, J 10.5 Hz, 4-H), 7.47 (1H, d, J 10.5 Hz, 6-H), 6.96 (1H, d, J 10.5 Hz, 7-H), 6.88 (1H, d, J 10.5 Hz, 3-H), 3.88 (3H, s, $OCH_3$); NMR Spectrum $\delta_C$ (75 MHz, $CDCl_3$) 57.0, 113.7, 116.2, 120.3; 123.9, 129.9, 135.8, 142.0, 149.1; $\nu_{max}$/cm$^{-1}$ (nujol mull) 3091, 2959, 2924, 2854, 1608, 1569, 1468, 1367, 1309, 1270, 1169, 1080, 909; $R_f$(hexane-ethyl acetate 1:1) 0.60.

To a suspension of copper bronze (0.646 g, 10 mmol) in anhydrous DMF (2 mL) was added a solution of 2-bromo-3,4,5-trimethoxybenzaldehyde (0.80 g, 2.91 mmol) and 3-bromo-2-formyl-6-methoxyphenyl methanesulfonate (0.30 g, 0.97 mmol) in anhydrous DMF (1 mL) and the suspension was stirred at 165° C. for 3 hours. TLC indicated the presence of unreacted 3-bromo-2-formyl-6-methoxyphenyl methanesulfonate and a further portion of 2-bromo-3,4,5-trimethoxybenzaldehyde (100 mg) was added. After a further 1 hour at 165° C. the reaction was complete and the reaction mixture was cooled and diluted with ethyl acetate (20 mL). The resulting suspension was filtered through Celite® (3 g) and the filtrate concentrated in vacuo. The residue was chromatographed over silica gel (70 g), eluting with hexane-ethyl acetate (gradient 2:1 to 1:1), followed by crystallisation (ethyl acetate) yielded 2,6'-diformyl-4,2',3',4'-tetramethoxybiphenyl-3-yl methanesulfonate (180 mg, 44%); m.p. 130-131° C.; Elemental Analysis Found: C, 53.7; H, 4.8; S, 7.8 ($C_{19}H_{20}O_9S$ requires C, 53.77; H, 4.75; S, 7.56%); NMR Spectrum $\delta_H$ (300 MHz, $CDCl_3$) 10.18 (1H, s, 2-CHO), 9.63 (1H, s, 6'-CHO), 7.36 (1H, s, 5'-H), 7.26 (1H, d, J 8.4 Hz, 6-H), 7.15 (1H, d, J 8.4 Hz, 5-H), 4.03 (3H, s, $OCH_3$), 3.98 (3H, s, $OCH_3$), 3.57 (3H, s, $OCH_3$), 3.43 (3H, s, $SCH_3$); NMR Spectrum $\delta_C$ (100 MHz, $CDCl_3$) 50.2, 56.5, 56.9, 61.2, 61.5, 106.2, 116.8, 127.5, 130.0, 130.7, 131.0, 132.1, 139.8, 147.6, 151.1, 152.6, 154.0, 189.3, 190.5; $\nu_{max}$/cm$^{-1}$ (thin film) 2934, 2843, 1701, 1682, 1588, 1561, 1480, 1371, 1336, 1285, 1169, 1111, 1072; m/z (ES) 447 ($MNa^+$, 100%), 379 (5); $R_f$(hexane-ethyl acetate 1:2) 0.20.

To a solution of 2,6'-diformyl-4,2',3',4'-tetramethoxybiphenyl-3-yl methanesulfonate (170 mg, 0.40 mmol) in methanol (4 mL) was added sodium borohydride (45 mg, 1.20 mmol) and the solution was stirred at room temperature for 1 hour. Water (20 mL) and ethyl acetate (20 mL) were added to the reaction, the layers were separated and the aqueous layer was extracted with ethyl acetate (2×20 mL). The combined extracts were dried over $Na_2SO_4$ and filtered. The solvent was removed in vacuo and the residue was purified by flash chromatography over silica gel (25 g), eluting with hexane-ethyl acetate (1:2), followed by crystallisation (ethyl acetate), which yielded 2,6'-bis(hydroxymethyl)-4,2',3',4'-tetramethoxybiphenyl-3-yl methanesulfonate as a white solid (164 mg, 96%); m.p. 124-126° C.; High Resolution Mass Spectrometry Found: M+Na$^+$ 451.1041 ($C_{18}H_{20}O_7Na$ requires 451.1039); NMR Spectrum $\delta_H$ (300 MHz, $CDCl_3$) 7.08 (1H, d, J 8.4 Hz, 6-H), 7.01 (1H, d, J 8.4 Hz, 5-H), 4.64 (1H, d, J 12.0 Hz, 2-$CH_A$OH), 4.26 (1H, d, J 12.0 Hz, 2-$CH_B$ OH), 4.18 (2H, dd, J 2.9, 11.8 Hz, 6'-$CH_2$OH), 3.94 (3H, s, $OCH_3$), 3.92 (3H, s, $OCH_3$), 3.88 (3H, s, $OCH_3$), 3.56 (3H, s, $OCH_3$), 3.40 (3H, s, $SCH_3$); NMR Spectrum $\delta_C$ (75 MHz, $CDCl_3$) 50.2, 56.5, 56.9, 61.2, 61.5, 106.2, 116.8, 127.5, 130.0, 130.7, 131.0, 132.1, 139.8, 147.6, 151.1, 152.6, 154.0, 189.3, 190.5; $\nu_{max}$/cm$^{-1}$ (thin film) 3219, 2947, 1607, 1484, 1410, 1363, 1328, 1278, 1161, 1111, 1006, 889; m/z (ES) 447 ($MNa_2H_2O^+$, 100%); $R_f$(hexane-ethyl acetate 1:2) 0.18.

EXAMPLE 4

3,9,10,11-Tetramethoxy-5,7-dihydrodibenzo[c,e]oxepin-4-yl disodium phosphate

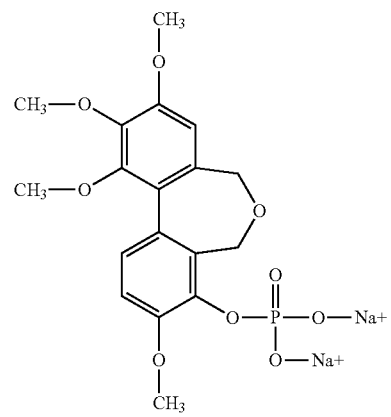

A mixture of 3,9,10,11-tetramethoxy-5,7-dihydrodibenzo [c,e]oxepin-4-yl dihydrogen phosphate (4.7 mg, 0.01146 mmol) and freshly prepared sodium methoxide solution, prepared from sodium (0.9 g) and methanol (100 mL) (0.585 mL, 0.023 mmol) was stirred at room temperature for 4 hours. The mixture was then concentrated in vacuo to afford the title compound as a white crystalline solid (4.9 mg, 94%); m.p. 212° C.; High Resolution Mass Spectrometry Found: M+Na$^+$ 456.0560 ($C_{18}H_{19}O_9PNa_2$ requires 456.0562); $v_{max}/cm^{-1}$ (thin film) 2937, 2855, 1595, 1101; NMR Spectrum $\delta_H$ (400 MHz, D$_2$O) 3.67 (3H, s, OCH$_3$), 3.80 (1H, d, J 11.8 Hz, 5-H or 7-H), 3.88 (3H, s, OCH$_3$), 3.90 (3H, s, OCH$_3$), 3.92 (3H, s, OCH$_3$), 3.97 (1H, d, J 11.8 Hz, 5-H or 7-H), 4.44 (1H, d, J 11.3 Hz, 5-H or 7-H), 5.39 (1H, d, J 11.3 Hz, 5-H or 7-H), 7.01 (1H, s, 8-H), 7.15 (1H, d, J 8.4 Hz, 2-H), 7.32 (1H, br d, J 8.4 Hz, 1-H); NMR Spectrum $\delta_C$ (100 MHz, D$_2$O) 56.34, 56.46, 60.05, 61.46, 61.65, 67.01, 99.99, 109.92, 113.23, 126.01, 126.45, 129.90, 131.16, 142.13, 149.87, 152.75; NMR Spectrum $\delta_P$ (160 MHz, D$_2$O)-2.78 (P); m/z (ES) 410 (M−2Na, 80%).

The 3,9,10,11-tetramethoxy-5,7-dihydrodibenzo[c,e]oxepin-4-yl dihydrogen phosphate starting material was prepared as follows:

Using a method that was based on the preparative method disclosed in Silverberg, L. J.; Dillon, J. L.; Vemishetti, P.; Tetrahedron Lett. 1996, 37, 771-774, a two-necked flask fitted with a Quickfit thermometer under argon containing 3,9,10, 11-tetramethoxy-5,7-dihydrodibenzo[c,e]oxepin-4-ol (Example 3, 0.166 g, 0.5 mmol) and N,N-dimethylaminopyridine (9.7 mg, 0.08 mmol) was diluted with anhydrous acetonitrile (3.1 mL) and cooled to −10° C. on an internal thermometer. Anhydrous carbon tetrachloride (0.24 mL) was then added followed by diisopropylethylamine (0.183 mL, 1.1 mmol) and the mixture was stirred for 1 minute. Dibenzyl phosphite (0.160 mL, 0.724 mmol) was then added and the mixture was stirred at −10° C. for 30 minutes. At this point TLC indicated the consumption of the organic starting materials. The mixture was quenched at this temperature with 0.5 M KH$_2$PO$_4$ (3 mL), allowed to warm to room temperature, and then extracted with ethyl acetate (4×3 mL). The combined organic phase was washed with water (2×2 mL) and brine (2 mL), dried (MgSO$_4$), filtered and concentrated in vacuo to afford a tanned gum (about 0.45 g). Column chromatography (10 g SiO$_2$; buffered with triethylamine), eluting with petroleum ether 60-80°—ethyl acetate (1:1) afforded 3,9,10,11-tetramethoxy-5,7-dihydrodibenzo[c,e]oxepin-4-yl bis(phenylmethyl) phosphate as a white solid (0.193 g, 65%); m.p. 135° C.; High Resolution Mass Spectrometry Found: M+H$^+$ 593.1943 ($C_{32}H_{34}O_9P$ requires 593.1940); $v_{max}/cm^{-1}$ (thin film) 2943, 2858, 1482, 1461, 1278; NMR Spectrum $\delta_H$ (400 MHz, CDCl$_3$) 3.66 (3H, s, OCH$_3$), 3.83 (1H, d, J 11.4 Hz, 5-H or 7-H), 3.89 (3H, s, OCH$_3$), 3.92 (3H, s, OCH$_3$), 3.95 (3H, s, OCH$_3$), 4.02 (1H, d, J 11.4 Hz, 5-H or 7-H), 4.39 (1H, d, J 12.3 Hz, 5-H or 7-H), 5.12 (1H, d, J 12.3 Hz, 5-H or 7-H), 5.12-5.27 (4H, m, OCH$_2$Ph), 6.74 (1H, s, 8-H), 7.03 (1H, d, J 8.6 Hz, 2-H), 7.30-7.40 (10H, m, benzyl ArH), 7.52 (1H, dd, J 1.3, 8.6 Hz, 1-H); NMR Spectrum $\delta_C$ (100 MHz, CDCl$_3$) 56.45, 56.52, 60.39, 61.34, 68.18, 70.12, 70.18, 109.10, 112.52, 127.41, 128.23, 128.50, 128.77, 128.90, 131.41, 153.40; NMR Spectrum $\delta_P$ (160 MHz, CDCl$_3$)-4.54 (P); m/z (CI, NH$_3$) 593 (MH$^+$, 10%); R$_f$ (petroleum ether 60-80°—ethyl acetate 1:1) 0.22.

3,9,10,11-Tetramethoxy-5,7-dihydrodibenzo[c,e]oxepin-4-yl bis(phenylmethyl) phosphate (39.4 mg, 0.067 mmol) in methanol (3 mL) was stirred with palladium on charcoal (10% w/w; 4 mg) under hydrogen for 2 hours at room temperature and pressure until TLC indicated the consumption of the starting material. The mixture was then passed through a small silica plug (0.5 cm depth in a Pasteur pipette) and concentrated to afford 3,9,10,11-tetramethoxy-5,7-dihydrodibenzo[c,e]oxepin-4-yl dihydrogen phosphate as a white crystalline solid (26.6 mg, 97%); m.p. 132° C.; High Resolution Mass Spectrometry Found: M+Na$^+$ 435.0826 ($C_{18}H_{21}O_9PNa$ requires 435.0821); $v_{max}/cm^{-1}$ (thin film) 2930, 2858, 1590, 1107; NMR Spectrum $\delta_H$ (400 MHz, CD$_3$OD) 3.56 (3H, s, OCH$_3$), 3.74 (3H, s, OCH$_3$), 3.76 (3H, s, OCH$_3$), 3.87 (3H, s, OCH$_3$), 3.82-3.87 (1H, m, 5-H or 7-H), 3.90-3.95 (1H, m, 5-H or 7-H), 4.34 (1H, apparent d, J 9.6 Hz, 5-H or 7-H), 5.12 (1H, apparent d, J 9.6 Hz, 5-H or 7-H), 6.86 (1H, s, 8-H), 7.12 (1H, d, J 8.7 Hz, 2-H), 7.42 (1H, br d, J 8.7 Hz, 1-H); NMR Spectrum $\delta_C$ (100 MHz, CD$_3$OD) 56.94, 57.01, 61.43, 61.72, 61.86, 68.82, 101.28, 110.55, 113.71, 127.80, 128.05, 129.71, 131.78, 132.69, 144.52, 152.19, 154.90; NMR Spectrum $\delta_P$ (160 MHz, CD$_3$OD)-3.52 (P); m/z (ES) 435 (MNa$^+$, 80%).

EXAMPLE 5

1,2,3-Trimethoxy-9-nitro-5,7-dihydrodibenzo[c,e] oxepine

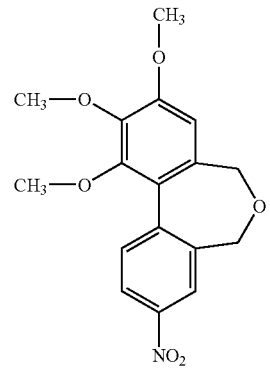

2'-Hydroxymethyl-4,5,6-trimethoxy-4'-nitrobiphenyl-2-yl)methanol (43.7 mg, 0.125 mmol) in 50% v/v aqueous sulfuric acid (1 mL) was heated in an oil bath of temperature 85° C. for 20 minutes. The mixture was cooled, quenched with ice (6 g) and extracted into chloroform (4×2 mL). The extract was dried (MgSO$_4$) and concentrated in vacuo to afford a dark tan solid. Column chromatography (petroleum ether 60-80°—ethyl acetate 2:1) afforded the title compound as a tan solid (39.6 mg, 96%); m.p. 161° C.; High Resolution Mass Spectrometry Found: M 331.1050 ($C_{17}H_{17}NO_6$ requires 331.1056); $v_{max}/cm^{-1}$ (thin film) 2935, 2856, 1597, 1518; NMR Spectrum $\delta_H$ (400 MHz, CDCl$_3$) 3.71 (3H, s, OCH$_3$), 3.95 (3H, s, OCH$_3$), 3.96 (3H, s, OCH$_3$), 3.97-4.03 (1H, m, 5-H or 7-H), 4.14-4.23 (1H, m, 5-H or 7-H), 4.39-4.48 (1H, m, 5-H or 7-H), 4.55-4.64 (1H, m, 5-H or 7-H), 6.78 (1H, s, 4-H), 7.89 (1H, d, J 8.2 Hz, 11-H), 8.28-8.32 (2H, m, 8-H and 10-H); NMR Spectrum $\delta_C$(100 MHz, CDCl$_3$) 56.53, 61.53, 61.56, 67.34, 67.93, 109.40, 123.33, 124.69, 125.09, 131.21, 131.93, 136.64, 143.14, 144.60, 147.19, 151.24, 154.85; m/z (ES) 331 (M, 45%); R$_f$ (petroleum ether 60-80°—ethyl acetate 2:1) 0.54.

The 2'-hydroxymethyl-4,5,6-trimethoxy-4'-nitrobiphenyl-2-yl)methanol starting material was prepared as follows:
A mixture of 2-bromo-3,4,5-trimethoxybenzaldehyde (prepared as described in Example 1, starting materials, 1.00 g, 3.64 mmol) and 2-chloro-5-nitrobenzaldehyde (obtained from Aldrich; 241.9 mg, 1.30 mmol) in dry DMF (2 mL) was added to a stirred, boiling suspension of copper bronze (0.91 g, 14.3 mmol) in dry DMF (5 mL) over a period of 30 minutes. After 8 hours TLC (petroleum ether-ethyl acetate 4:1) indicated the consumption of the starting materials. The mixture was cooled, passed through a Celite plug and diluted with toluene, which was distilled off to afford a dark oil. Column chromatography (petroleum ether 60-80°—ethyl acetate 2:1) afforded a sample of 4,5,6-trimethoxy-4'-nitrobiphenyl-2,2'-dicarbaldehyde (259 mg) containing traces of a second compound. This mixture was dissolved in ethanol (5 mL) and treated with a solution of sodium borohydride (0.2 g) in water (1.5 mL). After stirring for 40 minutes, the mixture was added to 1 M aqueous hydrochloric acid (20 mL). The precipitated product was collected on a filter, washed with water and recrystallised from ethanol, which gave the 2'-hydroxymethyl-4,5,6-trimethoxy-4'-nitrobiphenyl-2-yl)methanol as a white powder (113 mg, 25%), which was used for further reaction without further purification.

EXAMPLE 6

9,10,11-Trimethoxy-5,7-dihydrodibenzo[c,e]oxepin-3-amine

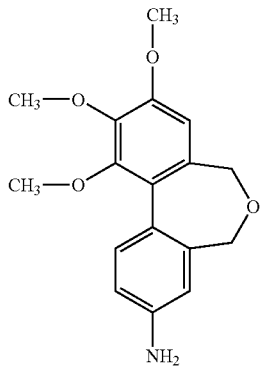

1,2,3-Trimethoxy-9-nitro-5,7-dihydrodibenzo[c,e]oxepine (Example 5, 85.4 mg, 0.258 mmol) in ethyl acetate (4 mL) containing palladium on charcoal (10% w/w; 7 mg) was stirred under a hydrogen balloon for 24 hours until TLC indicated the consumption of starting material. The mixture was passed through a plug of neutral alumina (0.5 cm depth in a Pasteur pipette) and concentrated in vacuo to afford the title compound as a yellow crystalline solid (70 mg, 91%); m.p. 145° C.; High Resolution Mass Spectrometry Found: M 301.1305 ($C_{17}H_{19}NO_4$ requires 301.1314); $v_{max}/cm^{-1}$ (thin film) 3461, 3361, 2938, 2852, 1607, 1482; NMR Spectrum $\delta_H$ (400 MHz, $CDCl_3$) 3.66 (3H, s, $OCH_3$), 3.78 (2H, br s, $NH_2$), 3.91 (3H, s, $OCH_3$), 3.94 (3H, s, $OCH_3$), 4.03-4.18 (2H, br m, 5-H or 7-H), 4.30-4.44 (2H, br m, 5-H or 7-H), 6.74 (1H, s, 8-H), 6.745 (1H, d, J 2.5 Hz, 4-H), 6.77 (1H, dd, J 2.5, 8.2 Hz, 2-H), 7.52 (1H, d, J 8.2 Hz, 1-H); NMR Spectrum $\delta_C$ (100 MHz, $CDCl_3$) 56.44, 61.12, 61.50, 68.11, 68.15, 109.08, 115.26, 116.12, 127.20, 127.47, 130.97, 131.34, 136.64, 143.09, 150.92, 152.79; m/z (ES) 301 (M, 20%); $R_f$ (petroleum ether 60-80°—ethyl acetate 2:3) 0.32.

EXAMPLE 7

3,9,10,11-Tetramethoxy-5,7-dihydrodibenzo[c,e]oxepin-4-yl trifluoromethanesulfonate

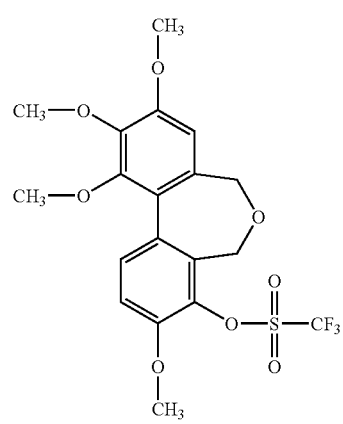

To a 5 mL flask containing 3,9,10,11-tetramethoxy-5,7-dihydrodibenzo[c,e]oxepin-4-ol (Example 3, 83.2 mg, 0.25 mmol) and anhydrous pyridine (0.283 mL, 3.50 mmol) in dry dichloromethane (0.3 mL) under argon was added trifluoromethanesulfonic anhydride (0.053 mL, 0.315 mmol) dropwise at 0° C. over a period of 2 to 3 minutes. After stirring the mixture at this temperature for 30 minutes, TLC indicated the consumption of starting material. The mixture was transferred to a separating funnel containing dichloromethane (2 mL) and 1 M hydrochloric acid (2 mL). The organic layer was collected and washed with more 1 M hydrochloric acid (2×1 mL), saturated aqueous sodium hydrogen carbonate (1 mL) and brine (0.5 mL), dried ($MgSO_4$), filtered and concentrated in vacuo to afford a dark yellow oil. Column chromatography (petroleum ether 60-80°—ethyl acetate 2:1) afforded the title compound as a white solid (90.6 mg, 85%); m.p. 164° C.; High Resolution Mass Spectrometry Found: M 464.0748 ($C_{19}H_{19}F_3O_8S$ requires 464.0753); $v_{max}/cm^{-1}$ (thin film) 2943, 2866, 1596, 1486, 1412, 1329; NMR Spectrum $\delta_H$ (400 MHz, $CDCl_3$) 3.68 (3H, s, $OCH_3$), 3.89-3.93 (1H, m, 5-H or 7-H), 3.93 (3H, s, $OCH_3$), 3.95 (3H, s, $OCH_3$), 3.98 (3H, s, $OCH_3$), 3.88-3.92 (1H, m, 5-H or 7-H), 4.43 (1H, d, J 11.1 Hz, 5-H or 7-H), 4.90 (1H, d, J 11.1 Hz, 5-H or 7-H), 6.74 (1H, s, 8-H), 7.12 (1H, d, J 8.3 Hz, 2-H), 7.63 (1H, d, J 8.3 Hz, 1-H); NMR Spectrum $\delta_C$ (100 MHz, $CDCl_3$) 56.49, 56.69, 60.19, 61.39, 61.50, 68.23, 98.49, 99.99, 109.21, 112.75, 125.22, 129.33, 130.40, 131.28, 137.15, 150.65, 150.96, 153.85; $\delta_F$ (375 MHz, $CDCl_3$) −77.98; m/z (EI) 464 (M, 10%); $R_f$ (petroleum ether 60-80°—ethyl acetate 2:1) 0.35.

EXAMPLE 8

3,9,10,11-Tetramethoxy-5,7-dihydrodibenzo[c,e]oxepine-4-thiol

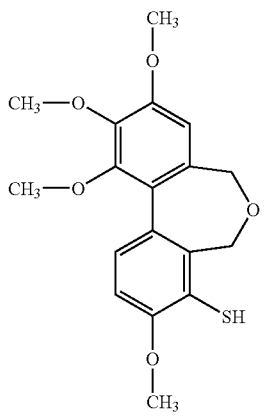

A mixture of 3,9,10,11-tetramethoxy-5,7-dihydrodibenzo[c,e]oxepin-4-yl trifluoromethanesulfonate (Example 7, 85.2 mg, 0.183 mmol), sodium hydrosulfide hydrate (41.7 mg, 0.743 mmol) and 2-pyrrolidinone (0.4 mL, 0.005 mmol) in a sealed tube was sonicated (Branson 1510, output 70 W) for a period of 10 minutes and then stirred at an oil bath temperature of 90° C. for 1 hour, which afforded a pungent yellow solid. Column chromatography (petroleum ether 60-80°—ethyl acetate 1:1) gave the title compound as a yellow gum (50 mg, 78%); $v_{max}$/cm$^{-1}$ (thin film) 2942, 2867, 2545, 1595, 1486; NMR Spectrum $\delta_H$ (400 MHz, CDCl$_3$) 3.76 (3H, s, OCH$_3$), 3.85 (1H, d, J 12.6 Hz, 5-H or 7-H), 3.92 (3H, s, OCH$_3$), 3.94 (3H, s, OCH$_3$), 3.96 (3H, s, OCH$_3$), 4.05 (1H, d, J 12.6 Hz, 5-H or 7-H), 4.40 (1H, d, J 11.9 Hz, 5-H or 7-H), 5.15 (1H, d, J 11.9 Hz, 5-H or 7-H), 5.86 (1H, s, SH), 6.78 (1H, m, 8-H), 6.94 (1H, d, J 8.5 Hz, 2-H), 7.21 (1H, d, J 8.5 Hz, 1-H); NMR Spectrum $\delta_C$ (100 MHz, CDCl$_3$) 56.44, 56.52, 59.65, 61.23, 61.52, 68.23, 109.17, 110.36, 121.23, 121.49, 126.85, 131.06, 131.56, 143.05, 143.80, 145.96, 151.07, 153.14; m/z (CI, NH$_3$) no molecular ion; R$_f$ (petroleum ether 60-80°—ethyl acetate 1:1) 0.32.

EXAMPLE 9

3,9,10,11-Tetramethoxy-5,7-dihydrodibenzo[c,e]oxepin-4-amine

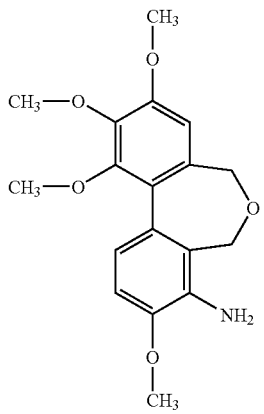

Using a method that was based on the preparative method disclosed in Wolfe, J. P.; Buchwald, S. L.; J. Org. Chem. 1997, 62, 1264-1267, a two-necked 5 mL flask with a reflux condenser and argon atmosphere was charged with palladium(II) acetate (91.7 mg, 0.008 mmol), (±)-BINAP (2.7 mg, 0.004 mmol) and sodium tert-butoxide (29.3 mg, 0.305 mmol) in dry toluene (0.5 mL). The mixture was heated under reflux and treated drop-wise with a solution of 3,9,10,11-tetramethoxy-5,7-dihydrodibenzo[c,e]oxepin-4-yl trifluoromethanesulfonate (Example 7, 96.7 mg, 0.208 mmol) and dry benzylamine (0.027 mL, 0.247 mmol) in dry toluene (1.5 mL) over a period of 15 minutes. The mixture was then heated under reflux for 5.5 hours, cooled and partitioned between ethyl acetate (3 mL) and water (1 mL). The phases were separated and the aqueous layer was extracted with ethyl acetate (1 mL). The combined organic phase was washed with brine (1 mL), dried (MgSO$_4$), filtered and concentrated in vacuo to afford a dark tan gum (about 120 mg). Column chromatography (SiO$_2$ buffered with 10% v/v triethylamine in the loading slurry), eluting with chloroform-methanol (49:1), afforded a fraction containing N-phenylmethyl-3,9,10,11-tetramethoxy-5,7-dihydrodibenzo[c,e]oxepin-4-amine and recovered starting material as a clear yellow gum (50 mg). This material was used without further purification in the next (hydrogenation) step.

The N-phenylmethyl-3,9,10,11-tetramethoxy-5,7-dihydrodibenzo[c,e]oxepin-4-amine (45.3 mg) and palladium on charcoal (10% w/w; 2.3 mg) in ethyl acetate (3 mL) in a steel autoclave was stirred under hydrogen (2 bar) for 2.5 hours. The mixture was then passed through a plug of alumina and concentrated in vacuo to afford a green oil. Column chromatography, eluting with chloroform-methanol 49:1), afforded the title compound as a pale orange gum (8.6 mg, 24%); High Resolution Mass Spectrometry Found: M+Na$^+$ 354.1319 (C$_{18}$H$_{21}$NO$_5$Na requires 354.1317); $v_{max}$/cm$^{-1}$ (thin film) 3364, 2946, 2850, 1599, 1572; NMR Spectrum $\delta_H$ (400 MHz, CDCl$_3$) 3.65 (3H, s, OCH$_3$), 3.88-3.90 (1H, m, 5-H or 7-H), 3.91 (3H, s, OCH$_3$), 3.92 (3H, s, OCH$_3$), 3.95 (3H, s, OCH$_3$), 3.95-3.98 (1H, m, 5-H or 7-H), 4.37 (1H, d, J 11.5 Hz, 5-H or 7-H), 4.70 (1H, d, J 11.5 Hz, 5-H or 7-H), 6.74 (1H, s, 8-H), 6.88 (1H, d, J 8.3 Hz, 2-H or 1-H), 6.94 (1H; d, J 8.3 Hz, 1-H or 2-H); NMR Spectrum $\delta_C$ (100 MHz, CDCl$_3$) 56.04, 56.31, 56.74, 56.85, 62.53, 71.48, 107.05, 114.42, 114.68, 118.32, 128.60, 129.76, 130.46, 131.96, 132.58, 146.78, 147.42, 147.53; m/z (ES) 331 (M, 100%); R$_f$ (chloroform-methanol 49:1) 0.18.

The invention claimed is:
1. A method for producing a vascular damaging effect in a warm-blooded animal comprising administering to a warm-blooded animal in need thereof an effective amount of a compound represented by Formula I:

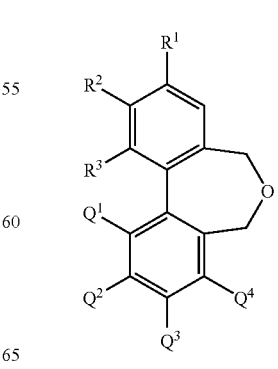

I or a pharmaceutically acceptable salt thereof wherein:

$R^1$, $R^2$ and $R^3$ each independently represent (1-4C)alkoxy;
$Q^1$, $Q^2$, $Q^3$ and $Q^4$ each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

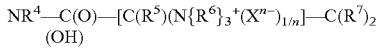

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or any one of $Q^2$ and $Q^3$ or $Q^3$ and $Q^4$ represents a methylenedioxy group;

and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents, provided that when $Q^1$ represents hydrogen or methoxy and $Q^4$ represents hydrogen, then $Q^2$ and $Q^3$ do not both represent methoxy.

2. The method of claim 1, wherein:
$Q^1$, $Q^2$, $Q^3$ and $Q^4$ each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, an alkali metal phosphato group, or a group of the formula:

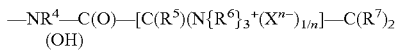

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or
any one of $Q^2$ and $Q^3$ or $Q^3$ and $Q^4$ represents a methylenedioxy group;
and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents.

3. The method of claim 1, wherein:
$Q^1$, $Q^2$, $Q^3$ and $Q^4$ each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

wherein $R^8$ and $R^9$ each independently represent hydrogen, hydroxy or (1-4C)alkoxy, or and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents.

4. The method of claim 1, wherein the vascular damaging effect is produced at least in part by inhibition of tubulin assembly into microtubules thereby interfering with cellular tubulin-microtubule equilibrium.

5. The method of claim 1, further comprising treating a disease or medical condition in which the damage of the vasculature in a warm-blooded animal has an effect.

6. The method of claim 1, further comprising treating a vascular proliferative disease or medical condition in a warm-blooded animal.

7. The method of claim 5, wherein the disease or medical condition is selected from one or more of a cancer, macular degeneration, proliferative retinopathy, psoriasis and/or endometriosis.

8. The method of claim 7, wherein the disease or medical condition is selected from a cancer, macular degeneration and/or proliferative retinopathy.

9. The method of claim 8, wherein the disease or medical condition is a cancer.

10. The method of claim 9, wherein the cancer is selected from one or more of leukaemias, colorectal, cervical, head and neck, lung, ovarian, pancreatic, thyroid, prostate, bladder, brain, breast, liver, stomach, oesophageal and/or skin cancers.

11. The method of claim 9, wherein the disease or medical condition is a cancer involving a solid tumour.

12. The method of claim 11, wherein the cancer is selected from one or more of colorectal, cervical, head and neck, lung, ovarian, pancreatic, thyroid, prostate, bladder, brain, breast, liver, stomach, oesophageal and/or skin cancers.

13. The method of claim 7, wherein the disease or medical condition is macular degeneration.

14. A compound represented by Formula I:

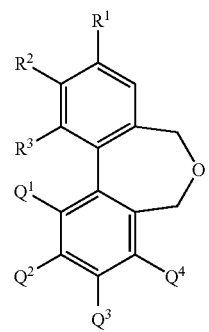

I or a pharmaceutically acceptable salt thereof
wherein:
$R^1$, $R^2$ and $R^3$ each independently represent (1-4C)alkoxy;
$Q^1$, $Q^2$, $Q^3$ and $Q^4$ each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

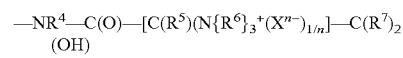

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

—$BR^8R^9$ wherein $R^8$ and $R^9$ each independently represent hydrogen, hydroxy or (1-4C)alkoxy, or any one of $Q^2$ and $Q^3$ or $Q^3$ and $Q^4$ represents a methylenedioxy group;

and wherein any $CH_2$ or $CH_3$ group within a $R^1$, $R^2$, $R^3$, $Q^1$, $Q^2$, $Q^3$ and/or $Q^4$ substituent optionally bears on each said $CH_2$ or $CH_3$ group one or more halogeno or hydroxy substituents;

provided that when $Q^1$ represents hydrogen or methoxy and $Q^4$ represents hydrogen, then $Q^2$ and $Q^3$ do not both represent methoxy.

15. The compound of claim 14, wherein:

$Q^1$, $Q^2$, $Q^3$ and $Q^4$ each independently represent hydrogen, halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, an alkali metal phosphato group, or a group of the formula:

—$NR^4$—C(O)—[C($R^5$)(N$\{R^6\}_3^+$($X^{n-})_{1/n}$]—C($R^7$)$_2$
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

—$BR^8R^9$ wherein $R^8$ and $R^9$ each independently represent hydrogen, hydroxy or (1-4C)alkoxy, or any one of $Q^2$ and $Q^3$ or $Q^3$ and $Q^4$ represents a methylenedioxy group;

and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy substituents;

provided that when $Q^1$ represents hydrogen or methoxy and $Q^4$ represents hydrogen, then $Q^2$ and $Q^3$ do not both represent methoxy.

16. The compound of claim 14, wherein:

$Q^1$, $Q^2$, $Q^3$ and $Q^4$ each independently represent hydrogen, halogeno, hydroxy, thiol, (2-4C)alkynyl, (1-4C)alkoxy, amino, (1-4C)alkylsulfonyloxy, an alkali metal phosphato group, or a group of the formula:

—$BR^8R^9$ wherein $R^8$ and $R^9$ each independently represent hydrogen, hydroxy or (1-4C)alkoxy, and wherein any $CH_2$ or $CH_3$ group within a $Q^1$, $Q^2$, $Q^3$ and/or $Q^4$ substituent optionally bears on each said $CH_2$ or $CH_3$ group one or more halogeno or hydroxy substituents;

provided that when $Q^1$ represents hydrogen or methoxy and $Q^4$ represents hydrogen, then $Q^2$ and $Q^3$ do not both represent methoxy.

17. The compound of claim 14, wherein $Q^1$ represents hydrogen.

18. The compound of claim 14, wherein $Q^4$ does not represent hydrogen.

19. The compound of claim 14, wherein the compound is represented by Formula I":

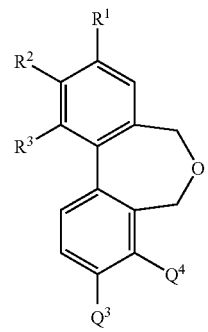

or a pharmaceutically acceptable salt thereof wherein:

$R^1$, $R^2$ and $R^3$ each independently represent (1-4C)alkoxy;

$Q^3$ and $Q^4$ each independently represent halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

$NR^4$—C(O)—[C($R^5$)(N$\{R^6\}_3^+$($X^{n-})_{1/n}$]—C($R^7$)$_2$
(OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

—$BR^8R^9$ wherein $R^8$ and $R^9$ each independently represent hydrogen, hydroxy or (1-4C)alkoxy, or $Q^3$ and $Q^4$ represent a methylenedioxy group;

and wherein any $CH_2$ or $CH_3$ group within a $R^1$, $R^2$, $R^3$, $Q^3$ and/or $Q^4$ substituent optionally bears on each said $CH_2$ or $CH_3$ group one or more halogeno or hydroxy substituents.

20. The compound of claim 19, wherein:

$Q^3$ and $Q^4$ each independently represent halogeno, hydroxy, thiol, (2-4C)alkynyl, (1-4C)alkoxy, amino, (1-4C)alkylsulfonyloxy, an alkali metal phosphato group, or a group of the formula:

—$BR^8R^9$ wherein $R^8$ and $R^9$ each independently represent hydrogen, hydroxy or (1-4C)alkoxy, and wherein any $CH_2$ or $CH_3$ group within a $Q^3$ and/or $Q^4$ substituent optionally bears on each said $CH_2$ or $CH_3$ group one or more halogeno or hydroxy substituents.

21. The compound of claim 14, wherein the compound is represented by Formula I''':

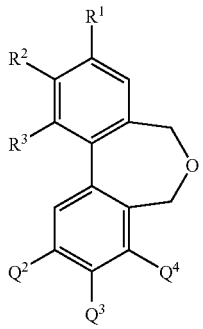

or a pharmaceutically acceptable salt thereof
wherein:
$R^1$, $R^2$ and $R^3$ each independently represent (1-4C)alkoxy;
$Q^2$, $Q^3$ and $Q^4$ each independently represent halogeno, hydroxy, cyano, nitro, trifluoromethyl, thiol, (1-4C)alkyl, (2-4C)alkenyl, (2-4C)alkynyl, (1-4C)alkoxy, amino, (1-4C)alkylamino, di-[(1-4C)alkyl]amino, (1-4C)alkylthio, (1-4C)alkylsulfonyl, (1-4C)alkylsulfonyloxy, an alkali metal phosphato group, or a group of the formula:

—NR⁴—C(O)—[C(R⁵)(N{R⁶}₃⁺(Xⁿ⁻)₁/ₙ]—C(R⁷)₂
     (OH)

wherein $R^4$, $R^5$, $R^6$ and $R^7$ each independently represent hydrogen, (1-4C)alkyl, (2-4C)alkenyl or (2-4C)alkynyl, $X^{n-}$ represents a suitable anion and n is 1 or 2, or a group of the formula:

—BR⁸R⁹ wherein $R^8$ and $R^9$ each independently represent hydrogen, hydroxy or (1-4C)alkoxy, or
any one of $Q^2$ and $Q^3$ or $Q^3$ and $Q^4$ represents a methylenedioxy group;
and wherein any $CH_2$ or $CH_3$ group within a $R^1$, $R^2$, $R^3$, $Q^2$, $Q^3$ and/or $Q^4$ substituent optionally bears on each said $CH_2$ or $CH_3$ group one or more halogeno or hydroxy substituents.

22. The compound of claim 21, wherein:
$Q^2$, $Q^3$ and $Q^4$ each independently represent halogeno, hydroxy, thiol, (2-4C)alkynyl, (1-4C)alkoxy, amino, (1-4C)alkylsulfonyloxy, an alkali metal phosphato group, or a group of the formula:

—BR⁸R⁹ wherein $R^8$ and $R^9$ each independently represent hydrogen, hydroxy or (1-4C)alkoxy,
and wherein any $CH_2$ or $CH_3$ group within a $Q^2$, $Q^3$ and/or $Q^4$ substituent optionally bears on each said $CH_2$ or $CH_3$ group one or more halogeno or hydroxy substituents.

23. The compound of claim 14, wherein $R^1$, $R^2$ and $R^3$ each independently represent (1-2C)alkoxy.

24. The compound of claim 23, wherein $R^1$, $R^2$ and $R^3$ each represent methoxy.

25. A compound of claim 14, selected from one or more of the following:
1,2,3,9-tetramethoxy-5,7-dihydrodibenzo[c,e]oxepine;
5,7-dihydro-1,2,3-trimethoxybenzo[d][1,3]dioxolo[4,5-h][2]benzoxepin;
3,9,10,11-tetramethoxy-5,7-dihydrodibenzo[c,e]oxepin-4-ol;
3,9,10,11-tetramethoxy-5,7-dihydrodibenzo[c,e]oxepin-4-yl disodium phosphate;
1,2,3-trimethoxy-9-nitro-5,7-dihydrodibenzo[c,e]oxepine;
9,10,11-trimethoxy-5,7-dihydrodibenzo[c,e]oxepin-3-amine;
3,9,10,11-tetramethoxy-5,7-dihydrodibenzo[c,e]oxepin-4-yl trifluoromethanesulfonate;
3,9,10,11-tetramethoxy-5,7-dihydrodibenzo[c,e]oxepine-4-thiol; and
3,9,10,11-tetramethoxy-5,7-dihydrodibenzo[c,e]oxepin-4-amine;
or a pharmaceutically acceptable salt thereof.

26. A method for the preparation of a compound of claim 14 or a pharmaceutically acceptable salt thereof, the method comprising reacting a compound represented by Formula II:

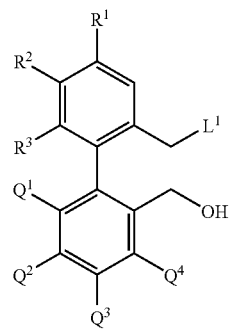

wherein $R^1$, $R^2$, $R^3$, $Q^1$, $Q^2$, $Q^3$ and $Q^4$ have any of the meanings defined in claim 14 except that any functional group is protected if necessary and $L^1$ is a suitable displaceable group, with a suitable ring closure reagent; and optionally,
(i) converting a compound represented by Formula I into another compound represented by Formula I; and/or
(ii) removing any protecting group that is present; and/or
(iii) forming a pharmaceutically acceptable salt.

27. A pharmaceutical composition comprising: a compound of claim 14 or a pharmaceutically acceptable salt thereof; and
(B) a pharmaceutically acceptable adjuvant, diluent or carrier.

28. The composition of claim 27, further comprising an additional anti-tumour agent for the conjoint treatment of a cancer.

* * * * *